(12) United States Patent
Sanders

(10) Patent No.: US 10,772,697 B2
(45) Date of Patent: Sep. 15, 2020

(54) ANATOMICAL DRAPE DEVICE

(71) Applicant: MAVRIK DENTAL SYSTEMS LTD., Ra'anana (IL)

(72) Inventor: Daniel Sanders, Ra'anana (IL)

(73) Assignee: MAVRIK DENTAL SYSTEMS, LTD., Ra'anana (IL)

(*) Notice: Subject to any disclaimer, the term of this patent is extended or adjusted under 35 U.S.C. 154(b) by 0 days.

(21) Appl. No.: 15/315,244

(22) PCT Filed: Jun. 1, 2015

(86) PCT No.: PCT/IB2015/054154
§ 371 (c)(1),
(2) Date: Nov. 30, 2016

(87) PCT Pub. No.: WO2015/186051
PCT Pub. Date: Dec. 10, 2015

(65) Prior Publication Data
US 2017/0252117 A1    Sep. 7, 2017

(30) Foreign Application Priority Data
Jun. 2, 2014 (GB) .................... 1409780.2

(51) Int. Cl.
*A61B 46/00* (2016.01)
*A61B 46/20* (2016.01)
(Continued)

(52) U.S. Cl.
CPC .............. *A61B 46/40* (2016.02); *A61B 46/20* (2016.02); *A61C 5/82* (2017.02); *A61C 19/003* (2013.01);
(Continued)

(58) Field of Classification Search
CPC .......... A61B 46/40; A61B 46/20; A61C 5/82; A61C 19/003; A61C 2202/01; A61C 5/12;
(Continued)

(56) References Cited

U.S. PATENT DOCUMENTS 741,890 A    10/1903 Craigie
1,579,608 A    4/1926 Haudenshield
(Continued)

FOREIGN PATENT DOCUMENTS

CH    421379    9/1966
CN    1225810 A    8/1999
(Continued)

OTHER PUBLICATIONS

Office Action from the United Kingdom Patent Office, Application No. GB1400767.8 dated Aug. 6, 2014.
(Continued)

*Primary Examiner* — Sean M Michalski
*Assistant Examiner* — Mirayda A Aponte
(74) *Attorney, Agent, or Firm* — The Dobrusin Law Firm, P.C.

(57) ABSTRACT

Disclosed is an anatomical drape, such as a dental drape, for covering a treatment area of an anatomical part. The drape includes an elastomeric material capable of conforming to the contours of the anatomical part. The drape preferably includes a curing agent. Activation of the curing agent, for example by a light source, causes selective hardening of the stretched material to at least partially set the drape in a configuration conforming to the anatomical part. The semi-rigid set drape preferably is liquid impermeable but gas permeable. A method of manufacturing the drape is also disclosed.

20 Claims, 14 Drawing Sheets

(51) Int. Cl.
*A61C 5/82* (2017.01)
*A61C 13/15* (2006.01)
*A61L 31/04* (2006.01)
*A61L 31/16* (2006.01)

(52) U.S. Cl.
CPC .............. *A61L 31/04* (2013.01); *A61L 31/16* (2013.01); *A61C 19/004* (2013.01); *A61C 2202/01* (2013.01); *A61L 2400/00* (2013.01)

(58) Field of Classification Search
CPC .... A61C 7/08; A61C 5/90; A61C 9/00; A61L 31/04; A61L 31/16; A61L 2400/00; A61F 2/02; A61F 5/566; A61F 2005/563; A61F 13/00038; C08F 20/00; A61M 16/0488; A61M 16/049; A61M 16/0493; A61M 16/0495
USPC .................. 433/136; 428/315.5, 316.6, 422; 427/245; 128/849, 859, 861, 862
See application file for complete search history.

(56) References Cited

U.S. PATENT DOCUMENTS

| | | | |
|---|---|---|---|
| 2,092,549 A | 9/1937 | Craigo | |
| 2,937,445 A | 5/1960 | Erickson | |
| 3,049,806 A | 8/1962 | Cofresi | |
| 3,481,329 A | 12/1969 | Warren | |
| 3,489,141 A | 1/1970 | Warren | |
| 3,527,218 A | 9/1970 | Westine | |
| 3,527,219 A | 9/1970 | Greenberg | |
| 3,536,069 A | 9/1970 | Gores | |
| 3,566,869 A | 3/1971 | Crowson | |
| 3,669,101 A | 6/1972 | Kleiner | |
| 3,727,309 A * | 4/1973 | Huey | A61C 13/00 433/171 |
| 3,731,675 A | 5/1973 | Kelly | |
| 3,742,942 A | 7/1973 | Westline | |
| 3,772,790 A | 11/1973 | Swan-Gett et al. | |
| 3,840,992 A | 10/1974 | English | |
| 4,059,101 A | 11/1977 | Richmond | |
| 4,106,501 A | 8/1978 | Ozbey et al. | |
| 4,138,814 A | 2/1979 | Weitzman | |
| 4,164,940 A | 8/1979 | Quinby | |
| 4,192,071 A | 3/1980 | Erickson | |
| 4,560,351 A | 12/1985 | Osborne | |
| 4,600,387 A | 7/1986 | Ross | |
| 4,983,381 A | 1/1991 | Zaragoza | |
| 4,990,089 A | 2/1991 | Munro | |
| 5,008,062 A * | 4/1991 | Anderson | B29C 45/14336 264/252 |
| 5,078,604 A * | 1/1992 | Malmin | A61C 5/82 433/136 |
| 5,104,315 A | 4/1992 | McKinley | |
| 5,365,624 A | 11/1994 | Berns | |
| 5,443,386 A | 8/1995 | Viskup | |
| 5,487,662 A | 1/1996 | Kipke et al. | |
| 5,513,986 A | 5/1996 | Feltham et al. | |
| 5,575,654 A | 11/1996 | Fontenot | |
| 5,682,904 A | 11/1997 | Stinnett | |
| 5,807,295 A * | 9/1998 | Hutcheon | A61F 5/01 602/42 |
| 6,077,073 A | 6/2000 | Jacon | |
| 6,152,733 A | 11/2000 | Hegemann et al. | |
| 6,254,391 B1 | 7/2001 | Darnell | |
| 6,343,932 B1 | 2/2002 | Wiesel | |
| 6,364,665 B1 | 4/2002 | Trettenero | |
| 6,439,889 B1 | 8/2002 | Chen et al. | |
| 6,616,447 B1 | 9/2003 | Rizoiu | |
| 6,893,259 B1 | 5/2005 | Reizenson | |
| 6,981,874 B2 | 1/2006 | Allred et al. | |
| 7,118,377 B2 | 10/2006 | Inoue et al. | |
| 7,331,784 B2 | 2/2008 | Suzuki | |
| 7,775,795 B2 | 8/2010 | Khawaled et al. | |
| 8,029,278 B1 | 10/2011 | Levine | |
| 8,205,618 B2 | 6/2012 | Berghash et al. | |
| 8,215,954 B2 | 7/2012 | Levine | |
| 8,277,215 B2 | 10/2012 | McLean et al. | |
| 2001/0038997 A1 | 11/2001 | Lindquist | |
| 2002/0110780 A1 | 8/2002 | Zegarelli | |
| 2002/0137001 A1 | 9/2002 | Cipolla et al. | |
| 2003/0104341 A1 | 6/2003 | Zavitsanos et al. | |
| 2004/0170945 A1* | 9/2004 | Heasley | A61C 5/82 433/136 |
| 2005/0037315 A1 | 2/2005 | Inoue et al. | |
| 2005/0196725 A1 | 9/2005 | Fu | |
| 2006/0029908 A1 | 2/2006 | Allred et al. | |
| 2006/0177796 A9 | 8/2006 | Heasley | |
| 2007/0015112 A1 | 1/2007 | Hochman et al. | |
| 2007/0178133 A1* | 8/2007 | Rolland | A61L 27/18 424/423 |
| 2007/0178420 A1* | 8/2007 | Keski-Nisula | A61C 7/08 433/6 |
| 2007/0184404 A1 | 8/2007 | Johnki | |
| 2007/0231773 A1* | 10/2007 | Pontynen | A61C 17/04 433/140 |
| 2007/0259316 A1 | 11/2007 | Conrad et al. | |
| 2008/0233541 A1 | 9/2008 | De Vreese et al. | |
| 2009/0087812 A1* | 4/2009 | Andersen | A61C 9/0006 433/37 |
| 2009/0123886 A1 | 5/2009 | Vaska | |
| 2011/0027746 A1 | 2/2011 | McDonough et al. | |
| 2011/0076636 A1 | 3/2011 | Wolff et al. | |
| 2011/0104633 A1 | 5/2011 | Levine | |
| 2011/0185525 A1 | 8/2011 | Stapelbroek et al. | |
| 2011/0189626 A1 | 8/2011 | Sanzari | |
| 2012/0156648 A1 | 6/2012 | Kaufman et al. | |
| 2017/0079746 A1 | 3/2017 | Sanders | |

FOREIGN PATENT DOCUMENTS

| | | |
|---|---|---|
| CN | 102036698 A | 4/2011 |
| DE | 871818 C | 3/1953 |
| WO | 2008/054312 A1 | 5/2008 |
| WO | 2009/146441 A1 | 12/2009 |
| WO | 2011/014619 A1 | 2/2011 |
| WO | 2013/039906 A1 | 3/2013 |
| WO | 2015/186051 A2 | 12/2015 |

OTHER PUBLICATIONS

Office Action from the Eurasian Patent Office, Application No. 201490628/31 dated Feb. 12, 2016.
International Search Report and Written Opinion, PCT/US2012/054652, dated Nov. 13, 2012.
International Preliminary Report on Patentability, PCT/US2012/054652, dated Mar. 12, 2014.
Goldberg et al., "Tooth Bleaching Treatments", L' eclaircissement dentaire—evaluation des therapeutiques, 2005 Association Dentaire Francaise, Paris, pp. 1-50; www.prgmea.com/docs/tooth/20.pdf.
International Search Report, Application No. PCT/IB2015/054154 dated Nov. 27, 2015.
Written Opinion, Application No. PCT/IB2015/054154 dated Nov. 27, 2015.
Extended European Search Report and Written Opinion, EP Application No. 15802387.9 dated Jan. 3, 2018.
Singapore Written Opinion, SG Application No. 112016099900 dated Sep. 25, 2017.
Chinese Office Action and Chinese Search Report, CN Application No. 201580039344.6 dated Jan. 29, 2018.
European Office Action for Application No. 12832113.0 dated Oct. 31, 2017.
Non-Final Office Action for U.S. Appl. No. 15/366,165 dated Jan. 11, 2018.
Japanese Office Action, JP Application No. 2016-570809 dated Mar. 19, 2019.

* cited by examiner

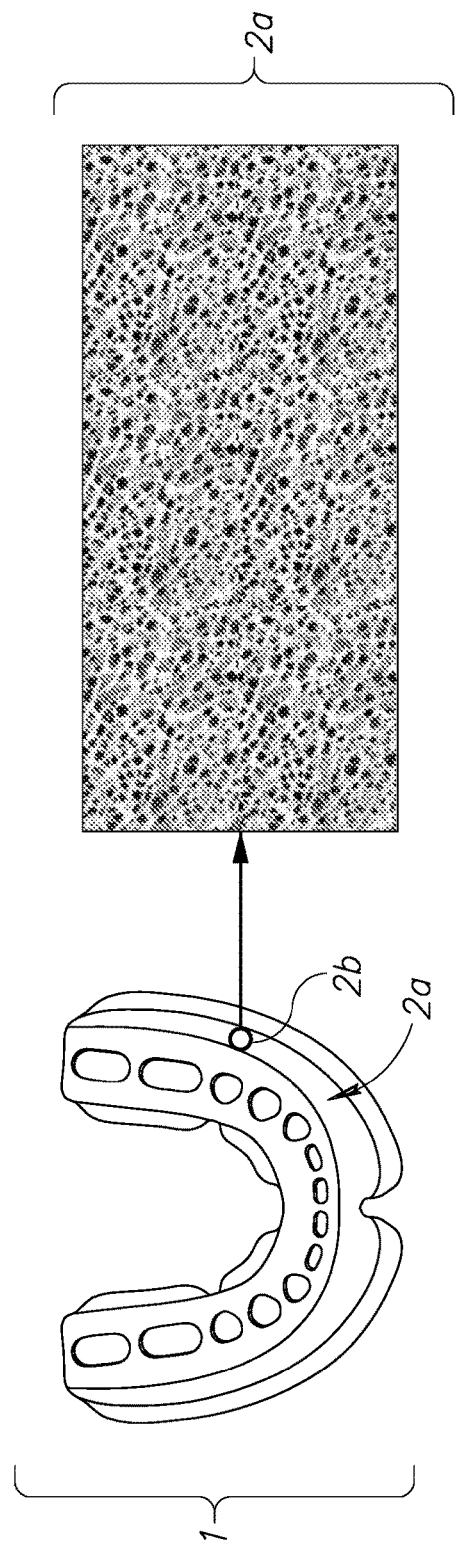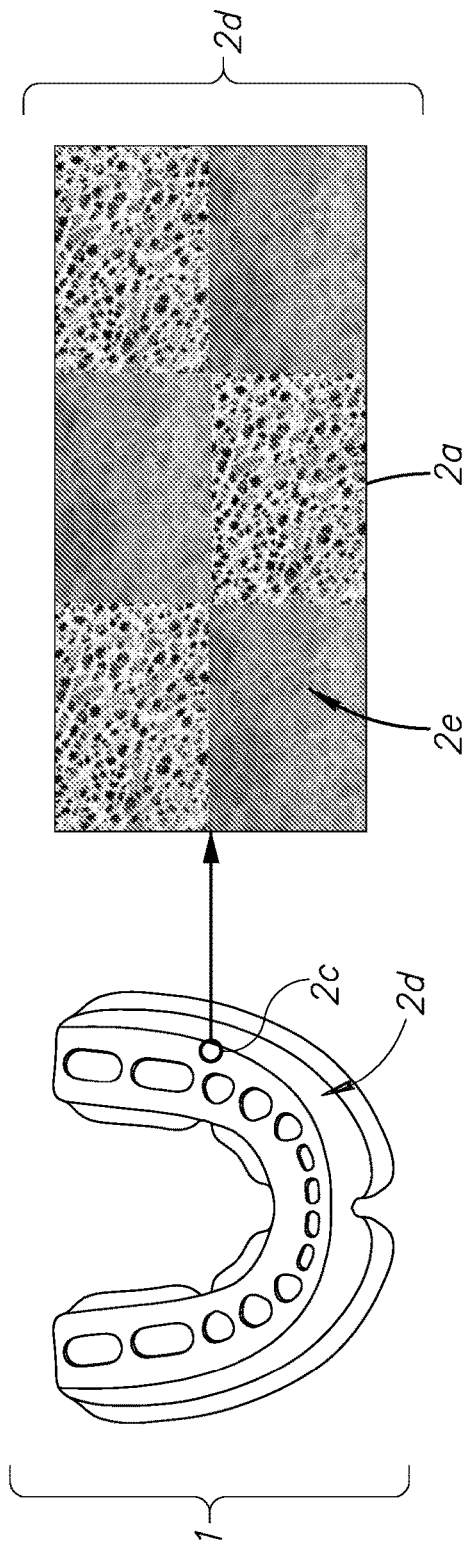

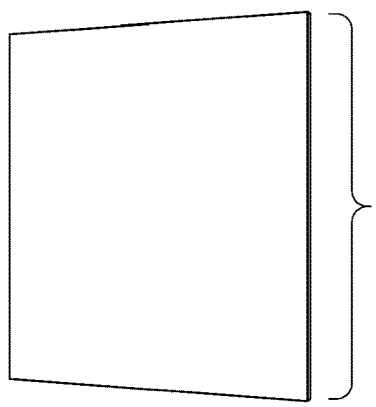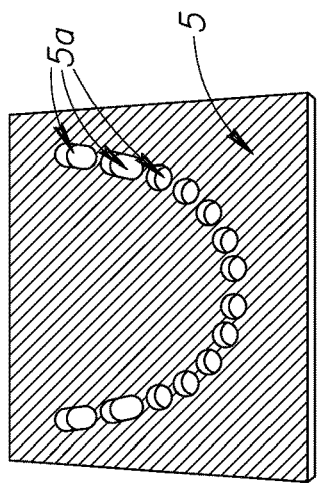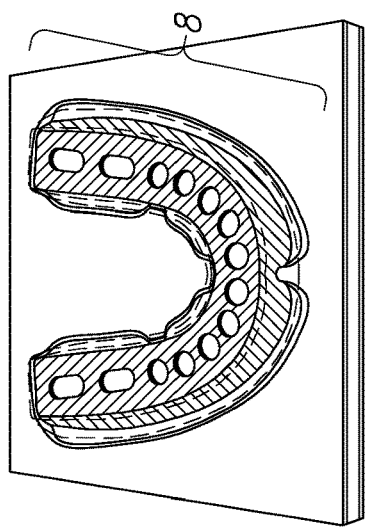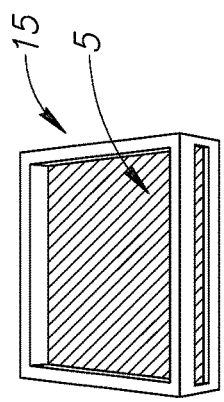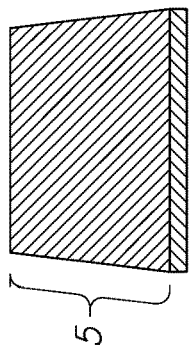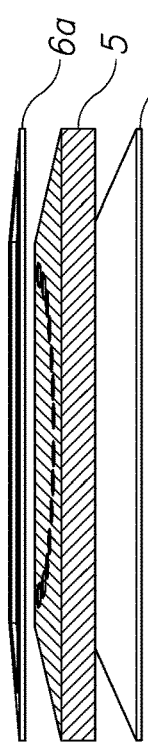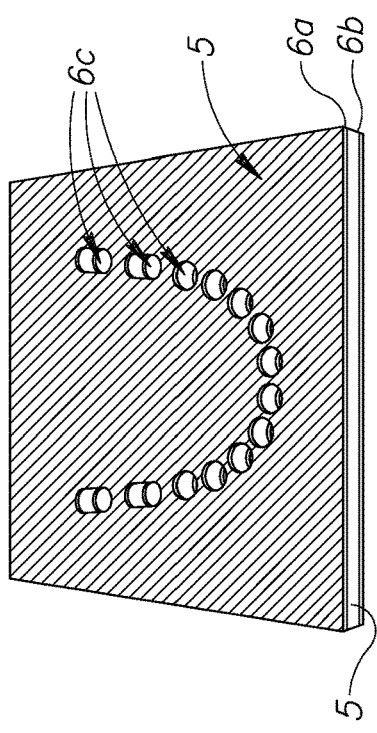

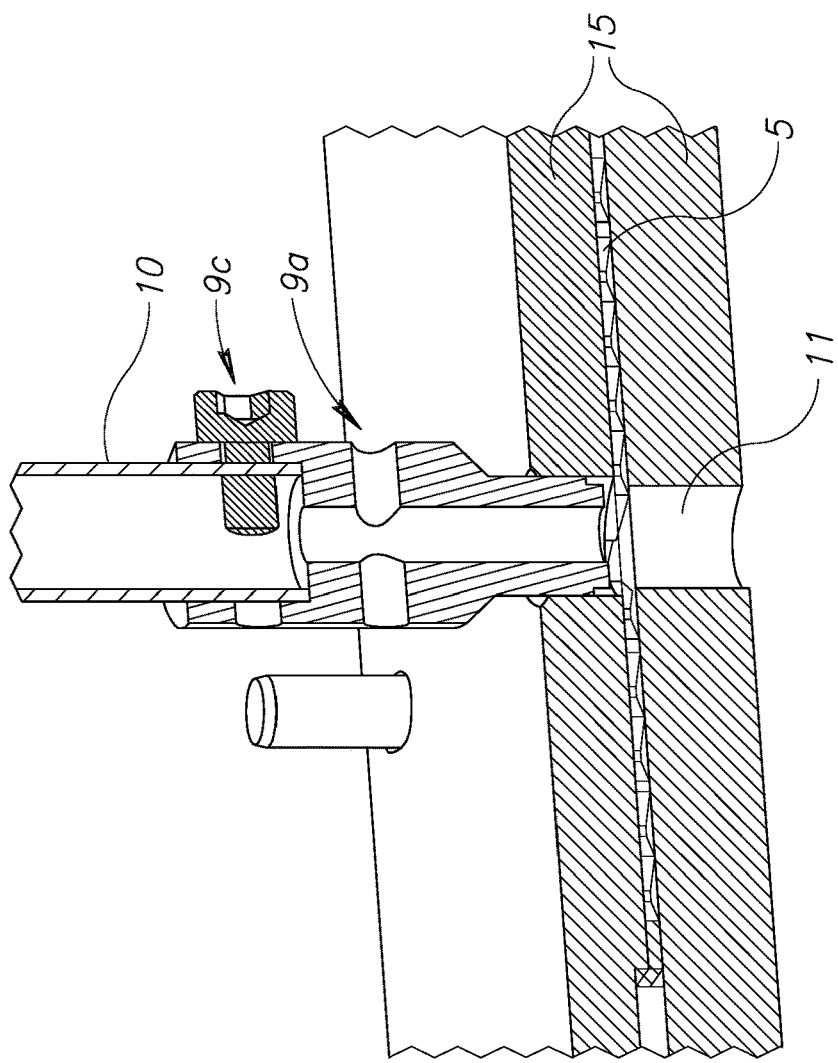
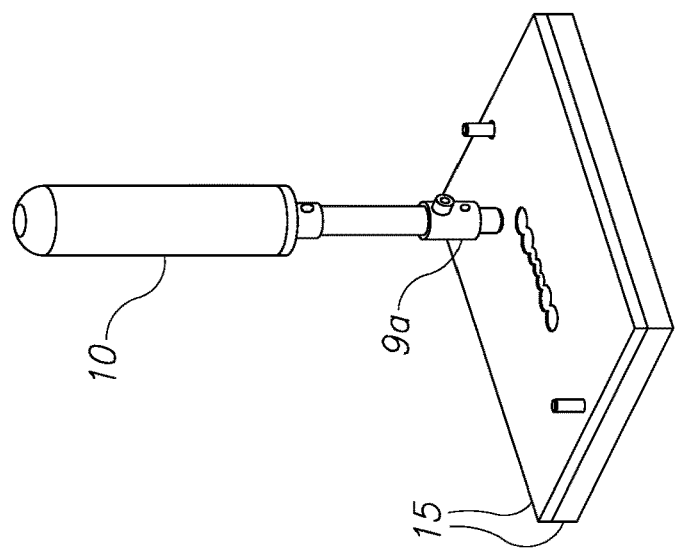
FIG.6B
FIG.6A

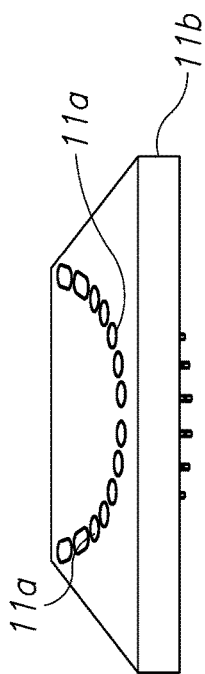
FIG.7F
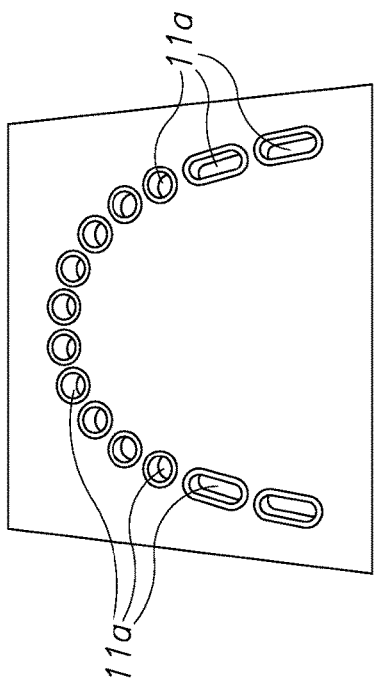
FIG.7D
FIG.7B
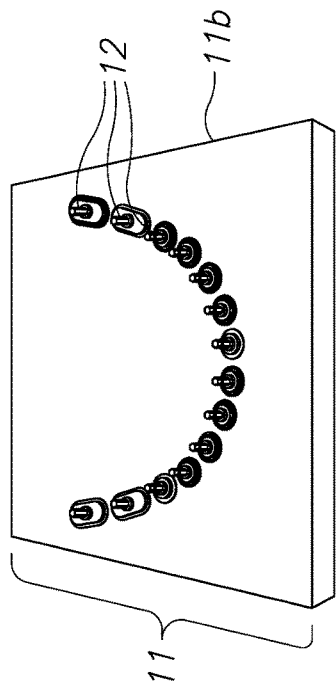
FIG.7E
FIG.7C
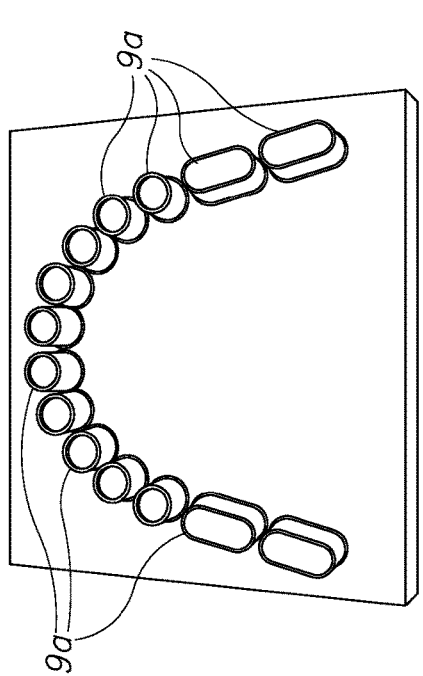
FIG.7A
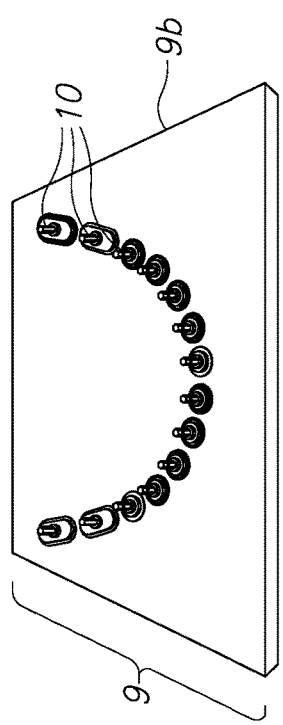

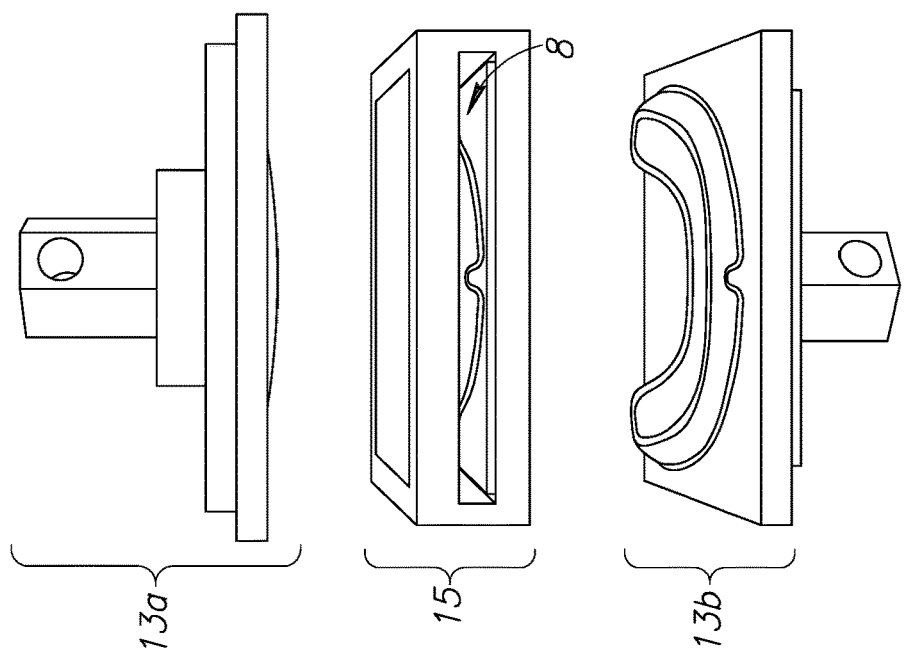
FIG.10B
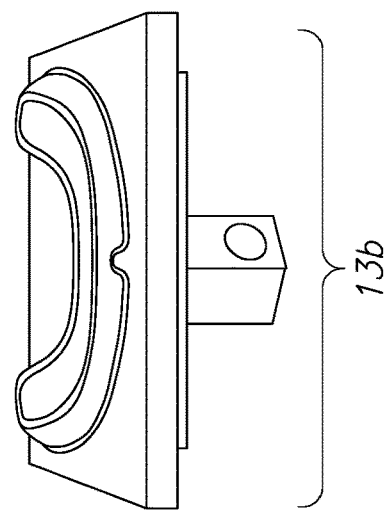
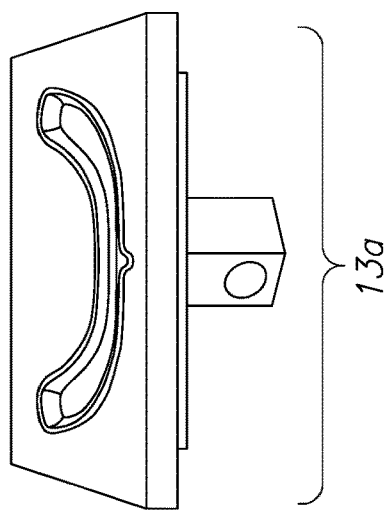
FIG.10A

ANATOMICAL DRAPE DEVICE

CLAIM OF PRIORITY

This application is a national phase filing under 35 USC § 371 of PCT Application serial number PCT/IB2015/054154 filed on Jun. 1, 2015, and claims priority therefrom. This application further claims priority to Great Britain Patent Application Number GB 1409780.2 filed on Jun. 2, 2014. PCT Application Number PCT/IB2015/054154 and Great Britain Patent Application Number 1409780.2 are each incorporated herein by reference in its entirety.

FIELD OF THE INVENTION

The present invention relates to methods and devices useful in providing drapes or covers for anatomical parts, such as during treatment of the parts, particularly but not exclusively to oral drapes for dental treatments.

BACKGROUND OF THE INVENTION

In dental medicine, many treatment materials are typically placed within the oral cavity on the hard (teeth) tissues and soft (inner mucosal epithelium of the cheek, lips, and gingiva and the tongue) tissues.

These treatment materials are placed topically on these tissues or may be inserted (injected) in the space between them, for example, in the naturally occurring sulcus at the tooth/gum line.

These treatment materials are typically applied to the tissues in an "open" manner, namely, without any covering material or containment device. This significantly reduces their desired therapeutic effect as the materials are immediately exposed to saliva contamination (containing numerous pathogenic microorganisms) and salivary washout (or fluid/solids ingestion washout) in a very short time. This time range can be as short as a few seconds to around 10 minutes or more, depending on salivary flow, the viscosity of the treatment material or whether the patient ingests solids or liquids after application of the treatment material.

Additionally, currently known devices use a cover device that covers both the teeth and the gums. These are typically custom made to a specific patient using the following fabrication method. Dental molds are taken of the patient's teeth and surrounding gums and dental stone cast models are poured and allowed to harden. These cast models are removed from the molds and a vacuum-formed thin plastic custom made tray for that specific patient is formed and trimmed to cover over both the teeth and a narrow portion of the surrounding gums. These typically leak the treatment material out of them and also allow saliva to seep inside of them as the stiff material of the tray is difficult to adapt closely to the undulating and varied topography of the teeth and surrounding gums of each individual patient which they are meant to cover. As these devices also cover the teeth, they generally do not allow the patient to eat or speak properly when they are inserted intraorally.

Additionally, patches onto whose inner surface a thin layer of treatment material has been adhered are used to cover small areas of the gum tissue. Due to their size they can only treat very limited areas of the soft tissues of the oral cavity and cannot be used to treat the teeth as they cannot be adhered to the teeth structure. They are also easily dislodged by the tongue or contact with the inner cheek and lip muscles.

It is an object of the present invention to provide an improved device that aims to overcome or at least alleviate the above mentioned drawbacks.

SUMMARY OF THE INVENTION

In accordance with a first aspect of the present invention, there is provided an anatomical drape for covering a treatment area of an anatomical part, the drape including an elastomeric material capable of conforming to the contours of the anatomical part and including a curing agent selectively incorporated within the drape structure, wherein activation of the curing agent selectively constrains the elastic properties of the stretched drape material to at least partially set the drape material in a fixed configuration conforming to the anatomical part.

In further embodiments, the elastomeric material of the drape is substantially liquid impermeable and gas permeable, both before and after curing.

In further embodiments, the drape is configured to generally conform to an oral anatomy.

In further embodiments, the drape conforms to a gum ridge anatomy with the drape forming an enclosed protective cover over the (entire) gum ridge with optional holes for passage of teeth there through.

In further embodiments, the curing agent is selectively positioned in the elastomeric material.

In further embodiments, the curing agent is positioned in one or more layers of the elastomeric material.

In further embodiments, the curing agent is activated by an external source selected from one or more of heat and light.

In further embodiments, the curing agent is a light curable agent selected from the group consisting of blended mixtures of acrylate monomers, urethane acrylate oligomers, triacrylate cross linkers, plasticizers, and photo-initiators.

In further embodiments, the anatomical drape is constructed from multiple layers.

In further embodiments, one or more treatment material layers are included on at least one surface of the drape.

In further embodiments, the curing agent is selectively activated by an external source selected from one or more of heat and light.

In further embodiments, a kits of parts is provided, for installing an anatomical drape, the kit comprising a drape as described above, and a light source, optionally with at least one further drape and/or a therapeutic or other treatment source.

In accordance with embodiments of the present invention, a method for the manufacture of an anatomical drape is provided, the method including the steps of: punching cut-out holes for the passage of teeth through a mesh layer of the anatomical mold; applying to both sides of the mesh layer one or more film-like outer layers; punching corresponding holes through both outer film-like layers; sealing the cut edges of the film-like outer layers, and heat setting all three layers into a desired three dimensional shape of the drape; punching and sealing the outer edges of the drape; and inserting a curable resin through the outer layer(s) and onto the middle mesh layer.

In further embodiments, the step of inserting a curable resin through the outer layer(s) and onto the middle mesh layer is performed after punching corresponding holes through both outer film-like layers and before heat setting all three layers into a desired three dimensional shape of the drape.

In further embodiments, the method further comprises packaging the product to protect uncured resin contained in the drape from setting.

In further embodiments, when punching or sealing the individual punching elements, the temperature is controlled to a specific range dependent on the size or shape of the hole to be punched and/or sealed.

In further embodiments, the insertion of the curable resin onto the mesh layer includes injecting through an in-port and allowing for the exit of excess curable resin through an out-port of the anatomical drape.

In accordance with embodiments of the present invention, an oral drape for covering a treatment area of an oral cavity is provided, the drape including an elastomeric material incorporated within the drape structure, capable of conforming to the contours of the oral anatomical part and including a curing agent wherein selective activation of the curing agent causes selective hardening of the material to at least partially set the drape in a configuration conforming to the anatomical part, the set drape being substantially gas permeable but liquid impermeable.

DESCRIPTION OF THE DRAWINGS

The principles and operation of the system, apparatus, and method according to the present invention may be better understood with reference to the drawings, and the following description, it being understood that these drawings are given for illustrative purposes only and are not meant to be limiting, wherein:

FIG. 2A is a top view of the lower full dental arch oral drape 1 of FIGS. 1C and 1D, wherein is depicted a delineated area of the weave-like spongy body surface 2a marked by a circle 2b, and further illustrated in an expanded view in FIG. 2B, according to some embodiments;

FIG. 2B is a magnified view of the microstructure of the oral drape 1, wherein are depicted a weave-lie spongy structure 2a that may include a myriad of three dimensional spongy threads and voids between the spongy threads;

FIG. 2C is a top view of the lower full dental arch oral drape 1 of FIGS. 1C and 1D, wherein is depicted a delineated area of the body surface 2a, marked by a circle 2c, according to some embodiments;

FIG. 2D is a magnified view of one embodiment of the microstructure of the oral drape 1, after partial impregnation of the second additive according to some embodiments;

FIG. 4A is a view of a layered material used to construct the drapes, according to some embodiments;

FIG. 4B is a view of layered material used to construct the drapes, according to some embodiments;

FIG. 4C is a view of an example of drape mold or shape for construction used for constructing drapes, in different stages, using the layered material, according to some embodiments;

FIG. 4D is a view of layered material used to construct the drapes, according to some embodiments;

FIG. 4E is a view of layered material used to construct the drapes, according to some embodiments;

FIG. 4F is a view of an example of drape mold or shape for construction used for constructing drapes, in different stages, using the layered material, according to some embodiments;

FIG. 4G is a view of an example of drape mold or shape for construction used for constructing drapes, in different stages, using the layered material, according to some embodiments;

FIG. 6A is a view of an illustrative process by which teeth holes are inserted into the drape mold, according to some embodiments;

FIG. 6B is a view of an illustrative process by which teeth holes are inserted into the drape mold, according to some embodiments;

FIG. 7A is a view of an illustrative drape mold with teeth holes in a stage of manufacture, according to some embodiments;

FIG. 7B is a view of an illustrative drape mold with teeth holes in a stage of manufacture, according to some embodiments;

FIG. 7C is a view of an illustrative drape mold with teeth holes in a stage of manufacture, according to some embodiments;

FIG. 7D is a view of an illustrative drape mold with teeth holes in a stage of manufacture, according to some embodiments;

FIG. 7E is a view of an illustrative drape mold with teeth holes in a stage of manufacture, according to some embodiments;

FIG. 7F is a view of an illustrative drape mold with teeth holes in a stage of manufacture, according to some embodiments;

FIG. 10A is a drawing showing views of examples of multiple layered drape molds being constructed using heat molding, according to some embodiments;

FIG. 10B is a drawing showing views of examples of multiple layered drape molds being constructed using heat molding, according to some embodiments;

DETAILED DESCRIPTION OF THE INVENTION

Figure 1C:
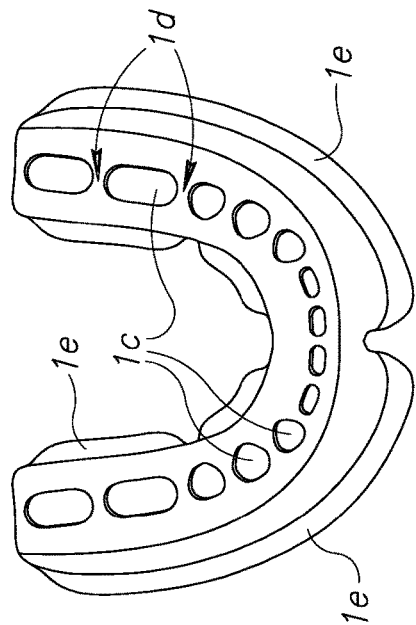
FIG. 1C is a is a top view of one embodiment of a lower full dental arch oral drape 1, according to some embodiments.

The following description is presented to enable one of ordinary skill in the art to make and use the invention as provided in the context of a particular application and its requirements. Various modifications to the described embodiments will be apparent to those with skill in the art, and the general principles defined herein may be applied to other embodiments. Therefore, the present invention is not intended to be limited to the particular embodiments shown and described, but is to be accorded the widest scope consistent with the principles and novel features herein disclosed. In other instances, well-known methods, procedures, and components have not been described in detail so as not to obscure the present invention.

The word "drape" as used herein may encompass various protective materials with or without adhesives that may be utilized to cover, dress or place over a target area or object(s) while undergoing a treatment, to cover or protect a target area, and optionally prevent the flow of liquids or materials from or to the target area.

In accordance with a first aspect of the present invention, there is provided an anatomical drape for covering a treatment area of an anatomical part, the drape comprising an elastomeric material capable of conforming to the contours of the anatomical part and including a curing agent incorporated within the structure, wherein selective activation of areas of the curing agent constrains the elastic properties of the stretched material of these areas of the drape in a fixed configuration conforming to the anatomical part.

The anatomical part preferably comprises an oral anatomy. However, it is to be appreciated that a drape may be provided to cover any anatomical part, such as a limb (or portion of a limb).

More preferably, the drape conforms to a gum ridge anatomy with the drape forming an enclosed protective cover over the entire gum ridge. The drape may comprise a partial or full U-shaped arch which is then tailored to the actual oral anatomy by sequentially constraining the individually stretched segments of the drape to provide a high level of conformity of each segment to the underlying anatomy of the tissue it covers. The drape, in some embodiments, may be provided with pre-perforated holes for easy removal and passage of teeth there-through or pre-configured cut-out holes may be provided of varying shapes and dimensions for receipt of teeth there-through whereby the teeth remain substantially uncovered and exposed to the oral cavity. The user may stretch sequentially different portions of the drape, and may sequentially constrain them by activating the curing agent contained within the drape's structure.

The preformed shape of the drape is formed to generally conform to the shape of the anatomical structures of the oral cavity and more specifically to the dentulous, partially edentulous or fully edentulous alveolar ridges of the oral cavity or other body part to facilitate easy and rapid insertion and removal of the drape from the target area.

The curing agent may only partially impregnate the elastomeric material, for example being scattered at intervals throughout the elastomeric material. It may also be limited to a specific layer of a multilayered structure of elastomeric materials. Upon polymerization of the curing agent, this may provide a semi-rigid drape that has been conformed to a particular individual anatomy while allowing its removal and enhancing comfort to the user.

Preferably, the elastomeric material of the drape is substantially liquid impermeable and gas permeable, both before and after curing. In some embodiments, the elastomeric material has high tear strength properties.

The drape may be comprised at least partially of an elastomeric material, to which has been added the curing agent. Any suitable curing agent may be used. In some embodiments the curing agent may be activated by an external source, such as heat and/or light.

Suitable elastomeric materials include, but are not limited to TPE's (thermoplastic elastomers); TPU's (thermoplastic urethanes); elastomeric silicones (RTV, HTV, LSR), the material preferably being both substantially liquid impermeable and gas permeable (i.e., breathable). Preferably, the material may contain millions of micro-pores per square cm.

In some embodiments, the drape may include one or more treatment material layers on at least one surface of the drape, for example for neutralizing treatment materials and/or gum treatment materials, such as therapeutic or medicinal agents.

The materials are preferably provided on the inner surface of the drape, but may be provided on the outer surface or in the internal layers of the drape.

In some embodiments, the drape may be comprised of at least three layers, wherein the two outer layers are comprised of film-like materials and a middle layer is comprised of a mesh type material of various pore sizes that has been impregnated with the curing agent. In such an embodiment of the drape, the two outer film-like materials of the drape may be suitable elastomeric materials that include but are not limited to TPE's (thermoplastic elastomers); TPU's (thermoplastic urethanes); elastomeric silicones (RTV, HTV, LSR), the material preferably being both substantially liquid impermeable and gas permeable (i.e., breathable). Preferably, the material contains millions of micro-pores per square cm, however other concentrations may be used. Further, in such an embodiment of the drape, the middle layer may be a mesh structure that may be comprised of suitable elastomeric materials that include but are not limited to TPP's (thermoplastic polypropylenes) TPET's (thermoplastic polyethylenes) or TPU's (thermoplastic urethanes), Polyamides such as Nylon or PA66, PA60, PA10, PA11, PA12.

Of course other materials are also available and may have suitable and even higher mechanical properties, such as PTFE (Teflon), Polybutylene terephthalate (PBT), Polyethylene (HDPE, LDPE, MDPE), Polyetheretherketone (PEEK), Polyvinyl Chloride (PVC), Polyurethane, silk, and even Metallic wires (stainless steel, Nitinol).

In some embodiments, the mesh material may be composed of multifilament or monofilament yarns. Monofilament is a single yarn, extruded and measured by its diameter or weight. Multifilament Yarn consisting of many strands that can be plied or twisted together. Multifilaments may have better conformity, be softer, and typically have higher tenacity than monofilament. In some examples, the mesh can range in filament diameter between 0.05 mm to 3.0 mm, with range of pore sizes such as between 0.05 mm to 3.0 mm, and weights such as between 10 to 200 gram square meters. Of course, other sizes and dimensions may be used.

In some embodiments, various mesh types may be used, varied by the production technique, including knitting (warp knitting, weft knitting etc.), weaving, braiding, and netting. Woven meshes generally have high tenacity, and may support precise specification structures and maintain a three dimensional structure. Their strength, porosity, morphology and geometry may be carefully defined. As opposed to other mesh structures whereas stretching capability and elasticity may be defined by an interplay between the pore geometry and the yarn materials properties, woven structures elasticity may be primarily defined by the yarns. Therefore, highly elastic woven meshes may be composed of elastic yarns, such as polyurethane or silicone, or thermoplastic elastomers.

In some embodiments, extruded netting may be used, manufactured through a single-step continuous extrusion process that yields a plastic material with integral joints. An extruder melts and pressurizes the plastic pellets and forces them through tooling in a die to create a netting profile. After the plastic moves through the die, it is cooled and the plastic hardens into the pre-determined shape. Netting configurations such as square, flat and diamond netting, extruded tubes, co-extrusion and bi-component netting may be used.

The mesh may be formed by extrusion or knitting in it various forms (e.g., warp knitted) and the diameter of the filaments and the pore size between the knitted or extruded filaments may vary based on the required application of the drape. Knitting typically involves intermeshing loops of yarn using higher number of individual fibers than most other textile engineering techniques, which allows for greater complexity and performance capabilities in created structures. Varied knitting techniques include warp knitting, weft knitting, and circular knitting. These knitting techniques allow different configurations such as increased strength per given thickness, increased flexibility, including mesh structures that allow cutting or other alteration without sacrificing edge integrity. Knitted mesh types may be used in medical device applications, including hernia mesh, urinary incontinence slings, pelvic organ prolapse suspenders and skin tissue.

In some embodiments, the mesh may be a fabricated by utilizing polypropylene, polyester or polyamide monofilaments. Filament count can range from 20 to 250 dTex, with 70 to 100 dTex preferred. One, two or three filament ends may be threaded through each feeder. The mesh may be warp knitted on a multi-bar Tricot machine with compound or bearded needles with gauge ranging from gauge E 10 to E 24, with gauges E 12 to E 18 preferred.

In some embodiments, an Atlas type structure may be used, such as Atlas Lapping. In the generation of this structure, the guide bar laps progressively in the same direction for a minimum of two consecutive courses, normally followed by an identical lapping movement in the opposite direction. The mesh has 5 to 20 courses per centimeter with 8 to 12 courses per centimeter preferred.

In some embodiments, the Mesh Technical Properties may include: Areal weight: 40 to 150 grams per square meter with 70 to 120 GSM preferred. Bursting strength>80 PSI. Thickness: 0.3 to 2 mm with 0.6 to 1 mm preferred. Pore dimensions: 0.5 to 2 mm across with 0.6 to 1.8 preferred. Void content: >40%, Initial heat set (strain relief): Heat-setting temperature depends on filament type. Between 85° C. to 120° C. for polypropylene, between 130° C. to 160° C. for polyester and between 105° C. to 130° C. for polyamide for a the time period between 60 to 300 seconds with between 60 to 180 seconds preferred. 3D heat set (shape retention): 3D heat-setting temperature depends on filament type typically in range between 105° C. to 140° C. For polypropylene, between 160° C. to 200° C.; for polyester between 115° C. to 160° C.; for polyamide for a the time period between 180 to 600 seconds with between 90 to 300 seconds preferred.

In accordance with some embodiments, the two outer film layers may prevent the penetration of liquids (such as hydrogen peroxide or saliva) onto the gums. Therefore, they may require low water vapor transmission rate (WVTR). Additionally, since, in some embodiments, they contain within the film packing a liquid light curing resin (LCR), they may be required to maintain a low diffusion coefficient of the LCR so as not to allow its leaching. Further, the film layers may need to be transparent so as to permit UV or visible light reaching the light curing resin.

In some embodiments, some of the most important mechanical properties required by the films are high strength, and maximal elongation, so they can be stretched 200% of their initial length without tearing. The high strength is required so they can be stretched by large applied force without tearing while having very thin profile (e.g. 30-50 micrometers). This may be obtained by using polyurethanes. In some cases, materials having low stretching properties, such as Polyethylene, PET and polypropylene, may not fit the implementation of embodiments of the invention.

In further embodiments, thermoplastic elastomeric (TPEs) types, elastomers (rubber) materials such as natural rubber, styrene butadiene rubber may be used, including generic classes of commercial TPE's such as Styrenic block copolymers (TPE-s), Polyolefin blends (TPE-o), Elastomeric alloys (TPE-v or TPV), Thermoplastic polyurethanes (TPU), Thermoplastic co-polyester, and Thermoplastic polyamides.

In accordance with one example, polyurethane film may be used for the drape material, wherein preferred properties for the anatomical drape include: Thickness (Micron) 30 micrometer; Weight (g/m$^2$) ~94; Tensile Strength MD (gf/cm) ~3000; Tensile Strength TD (gf/cm) ~3000; Elongation at break, MD (%) ~700; and Elongation at break, TD (%) ~700.

In further examples, instead of a film structure, the mesh may be coated using a dip-coating technique. An example of thermoplastic polyurethane solution dip coating may include using Lubrizol Tecoflex series in a stretched and non-stretched mode.

In further examples, Liquid Curable Resin (LCR) options may include: Potential light curing resin for anatomical drape application using off-the shelf dental adhesives, and light curing adhesives used in electronic and micro-electronic assemblies. The LCR should be configured to cure when exposed to light for a transient amount of time, for example, a few seconds. In some embodiments, the LCR may have the following properties: Curable with blue visible light source (1 W/cm2), wavelength: 420-480 nm; Curing time between 5 and 20 sec; Viscosity: minimum 4,000 cps maximum 50,000 cps; Certain adhesion to polypropylene; Should have enough processing time when exposed to room temperature conditions of 20 minutes (25° C., fluorescence light), noting that thermal degradation of the resin is less important if the production process considers that the LCA would not tolerate heat and light during production and certainly not during service during teeth whitening procedure; Reaction Temperature <40° C.; Minimal shelf life of 2 years at 4° C.; Post Cure Requirements: Fluxural strength ~80 MPa, Modulus of elasticity ~3,200 MPa; and Low cost materials/production.

In some embodiments, adhesives may be used that are suitable in medical applications and may be activated by light are light curing cyanoacrylate, acrylic, and urethane acrylate adhesives. In order to obtain the high strength in terms of modulus and strength, fillers may be incorporated into the monomer/oligomer formulation such as silica, or other non-reactive ceramic particles.

In some embodiments, Acrylics based basic MMA/PMMA mixtures may be used, which may be activated by photo chemical initiators, as are widely used in dental and other medical applications. For example, a variety of di- or multimethacrylates which are photo and/or chemically cured may be used. In some example, when cured in ambient temperature, free radicals may convert the resin to a cross linked free dimensional polymer network. The polymerizable photo-initiators may be soluble in the starting monomer and should be resistant to high temperatures; they should preferably react completely during the polymerization process and thereby prevent the formation of migratable photolytically degraded products with a strong odor after visible light irradiation. The extent of cure may also affects the mechanical properties, therefore resins may be used that enable formation of workable rheologies and hardening in several minutes, forming a tough and rigid plastic. In addition, such curing may enable substantially perfect transmission of visible light and excellent matrix forming potential.

According to some embodiments, Acrylic based adhesives offer the significant benefit of rapid curing in a time frame of 5 seconds. One example of acrylic based adhesive is Bis-GMA (2,2-bis[4-(2-hydroxy-3-methacryloyloxyprop-1-oxy)-phenyl]propane, bisphenol-A glycidyl ether dimethacrylate) and TEGDMA (triethyleneglycol dimethacrylate) monomers. These monomers are widely used matrices in dental restorative materials and teeth bonding agents. Dental adhesives based on TEGDMA/Bis-GMA present high stability, good physical and mechanical properties defined by the degree of cure, degree of polymerization.

Figure 1D:
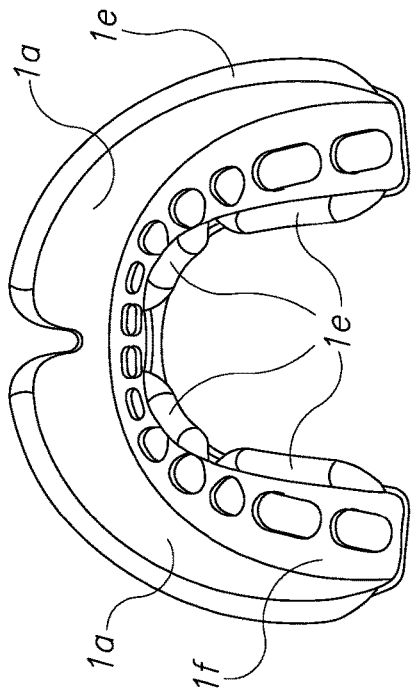
FIG. 1D is a bottom view of the lower full dental arch oral drape 1 of FIG. 1C, wherein are depicted the same features as in FIG. 1C, according to some embodiments.
Figure 1A:
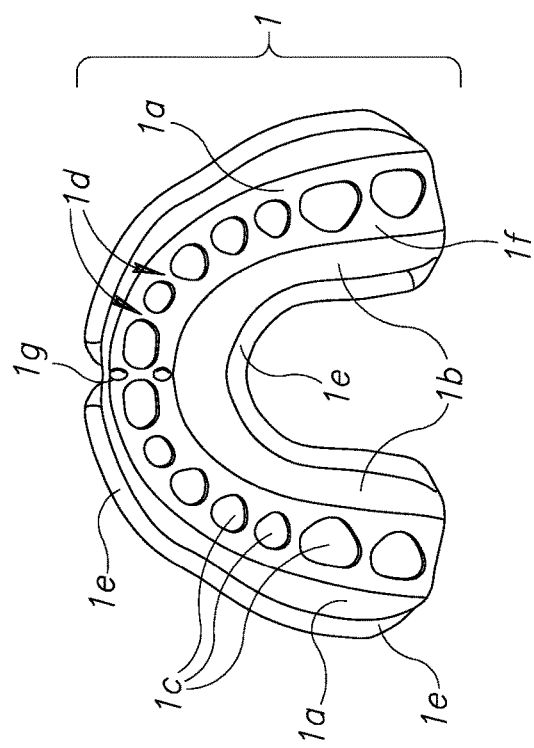
FIG. 1A is a top view of an upper full dental arch oral drape, according to some embodiments.

FIG. 1A is a top view of an upper full dental arch oral drape 1, according to some embodiments, wherein are depicted the buccal side wall 1a of the drape 1, the lingual side 1b of the drape 1, and the varying size and diameter holes 1c which allow the drape 1 to be placed over the teeth (so as to allow the teeth to remain substantially not covered by the oral drape and exposed to the oral cavity) and fitted over the surrounding gums to substantially cover them. Also depicted are the interdental tension bridges 1d which fit into the interproximal spaces (e.g. flossing areas) between adjacent teeth and provide a circumferential fit of the drape 1 around the teeth, the discontinuous outer rim roll 1e, which may stiffen to a degree the form of the oral drape and may aid in grasping its edges to facilitate its insertion onto the target treatment area. Also depicted is the crestal gum ridge surface 1f, and the midline reference bumps 1g, to visually and tactilely aid in positioning and alignment of the oral drape to the target treatment area.

Figure 1B:
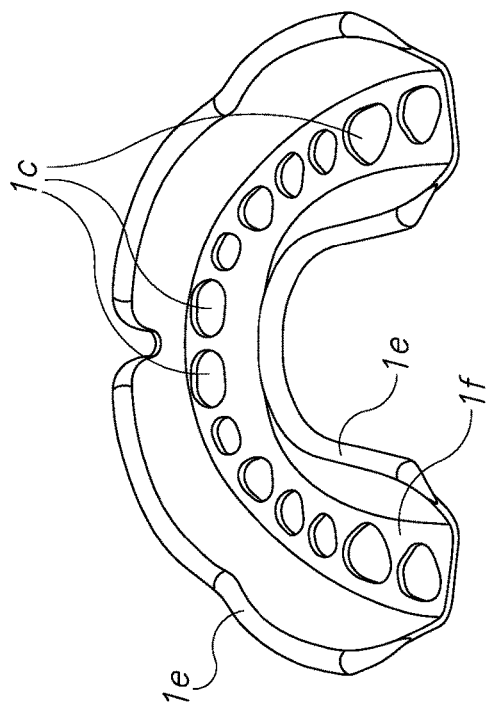
FIG. 1B is a bottom view of the upper full dental arch oral drape 1 of FIG. 1A, wherein are depicted the same features as in FIG. 1A, according to some embodiments.

FIG. 1B is a bottom view of the upper full dental arch oral drape 1 of FIG. 1A, wherein are depicted the same features as in FIG. 1a, according to some embodiments.

FIG. 1C is a is a top view of one embodiment of a lower full dental arch oral drape 1, according to some embodiments, wherein are depicted the buccal side wall 1a of the drape 1, the lingual side 1b of the drape 1, and the varying size and diameter holes 1c which allow the drape 1 to be placed over the teeth (so as to allow the teeth to remain substantially not covered by the oral drape and exposed to the oral cavity) and fitted over the surrounding gums. Also depicted are the interdental tension bridges 1d, the discontinuous outer rim roll 1e, the crestal gum ridge surface 1f, and the midline reference bumps 1g.

FIG. 1D is a bottom view of the lower full dental arch oral drape 1 of FIG. 1C, wherein are depicted the same features as in FIG. 1C, according to some embodiments.

FIG. 2A is a top view of the lower full dental arch oral drape 1 of FIGS. 1C and 1D, wherein is depicted a delineated area of the weave-like spongy body surface 2a marked by a circle 2b, according to some embodiments.

FIG. 2B is a magnified view of the microstructure of the oral drape 1, wherein are depicted one possible embodiment of a weave-lie spongy structure 2a that may include a myriad of three dimensional spongy threads and voids between the spongy threads, according to some embodiments.

FIG. 2C is a top view of the lower full dental arch oral drape 1 of FIGS. 1C and 1D, wherein is depicted a delineated area of the body surface 2a, marked by a circle 2c, according to some embodiments.

FIG. 2D is a magnified view of one embodiment of the microstructure of the oral drape 1, according to some embodiments, wherein are depicted a light curable material 2e, impregnated into portions of the weave-lie spongy structure 2a so as to form a pattern (e.g. a scatter pattern)

surface 2d composed of areas that are impregnated with curable material 2e and ones that are not impregnated with the curable material 2e.

Figure 3C:
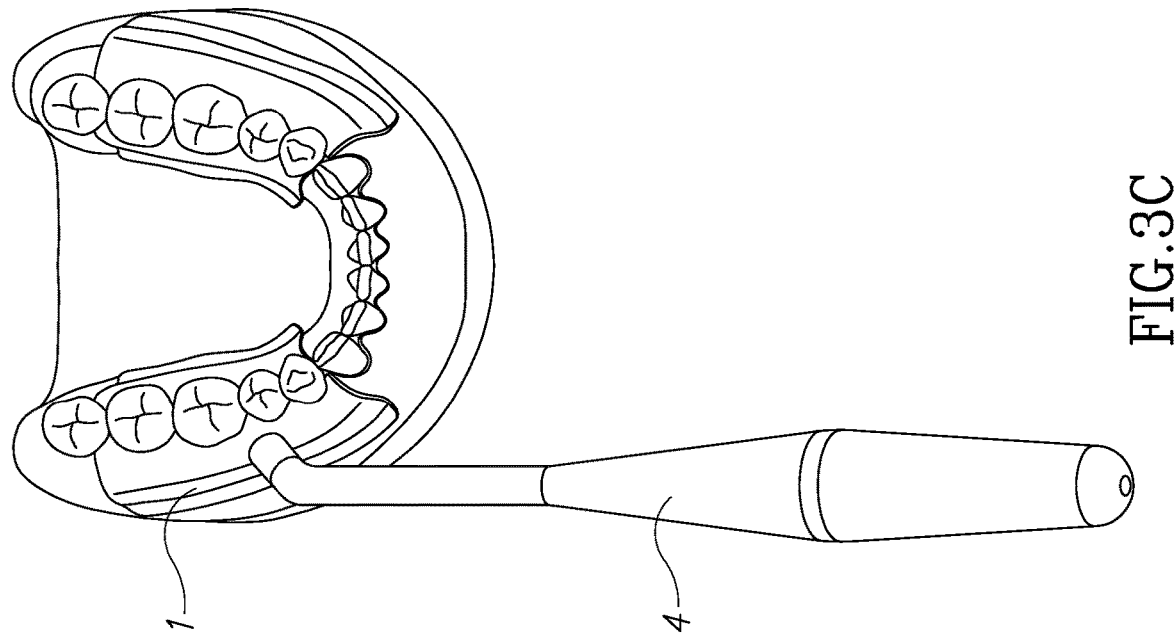
FIG. 3C is the top view of illustrated in FIG. 3B wherein is depicted a light source 4, directed to catalyze and so harden the impregnated curable material 2e, according to some embodiments.
Figure 3A:
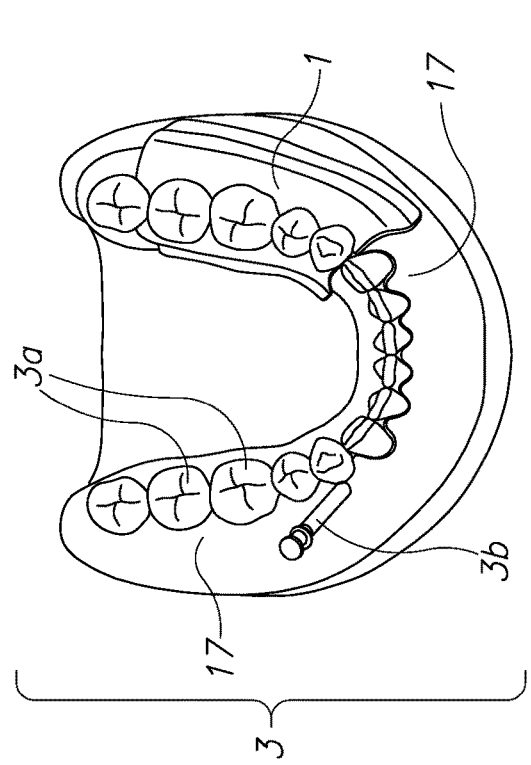
FIG. 3A is a top view of a lower full dental arch 3 which depicts the teeth 3a of the arch 3, according to some embodiments, of a segmental oral drape 1, and a syringe for the applying of medicinal therapeutics to the teeth 3a, the surrounding gums 5, or both.

FIG. 3A is a top view of a lower full dental arch 3 which depicts the teeth 3a of the arch 3, according to one embodiment, of a segmental oral drape 1, and a syringe 3b for the applying of therapeutics to the teeth 3a, the surrounding gums 17, or both prior to the placement of an oral drape 1 over this area.

Figure 3B:
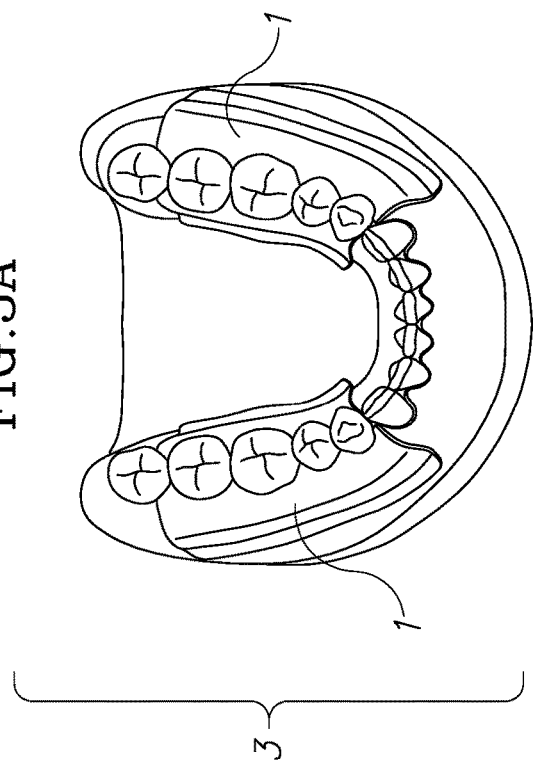
FIG. 3B is the top view illustrated in FIG. 3A, wherein is depicted a second segmental oral drape 1 fitted over the teeth and their surrounding gums 5 so as to cover over and contain the treatment material previously applied in FIG. 3A, according to some embodiments.

FIG. 3B is the top view illustrated in FIG. 3A, wherein is depicted a second segmental oral drape 1 fitted over the teeth and their surrounding gums 17 so as to cover over and contain the treatment material previously applied in FIG. 3A, according to some embodiments.

FIG. 3C is the top view of illustrated in FIG. 3B wherein is depicted a light source 4, directed to catalyze and so harden the impregnated curable material 2e, and so conform the oral drape 1 to the specific topography of the target treatment area and set in place the conformed oral drape 1 over the target treatment area, according to some embodiments. In some embodiments the curing agent may be selectively incorporated within the drape structure, such that activation of the curing agent selectively constrains the elastic properties of the stretched drape material to at least partially set the drape material in a fixed configuration conforming to the anatomical part. In further embodiments the curing agent may be selectively positioned and/or activated in the elastomeric material.

FIGS. 4A, 4B, 4C, 4D, and 4E are views of layered materials that may be used to construct the drapes, according to some embodiments. As can be seen, particularly in FIG. 4E, multiple layers may be used in the drape construction materials. In some embodiments, the outer layers may be films 6, being optionally breathable or non-breathable. As can be seen, upper film layer 6a and lower film layer 6b may surround a middle layer 5, which in some embodiments may include a curing agent. As can be seen, middle layer 5 may be constructed from one or more types or combinations of types of mesh material(s).

In some embodiments, the middle layer 5, and/or one or more of the outer layers 6a and 6b may incorporate a curing agent or material. In still further embodiments the curing agent may be selectively incorporated within the drape structure, such that activation of the curing agent selectively constrains the elastic properties of one or more layers of the stretchable drape material to at least partially set the drape material in a fixed configuration conforming to an anatomical part.

FIGS. 4F and 4G are views of examples of drape molds or shapes for construction used for constructing drapes, in different stages, using the layered materials, according to some embodiments. As can be seen, cut out holes 5a may be produced on mesh layer 5. Further cut out holes 6c may be produced on film layers 6. According to some embodiments, the holes may be first punched into the mesh layer 5 (optionally using multiple punches for multiple drapes on a big sheet of material, or other methods, and optionally using heat), before the films have been attached, to help prevent catalisation of the resin in the mesh layer when receiving heat from the punch hole production. After the mesh layer has holes punched into it, the outer films 6a and 6b may be attached, optionally using a heated puncher to punch and seal/weld the holes made into films 6a and 6b, so resin to be entered either at this stage or a later stage may substantially not leak out. In FIG. 4G the three layers may be thermally formed into the desired form, to form an initial three dimensional drape form 8. In some applications different heat settings for different size holes/punches may be used, to attain sealing of the punch holes in drape forms to be produced without diminishing from their ability to stretch and retract.

Figure 5B:
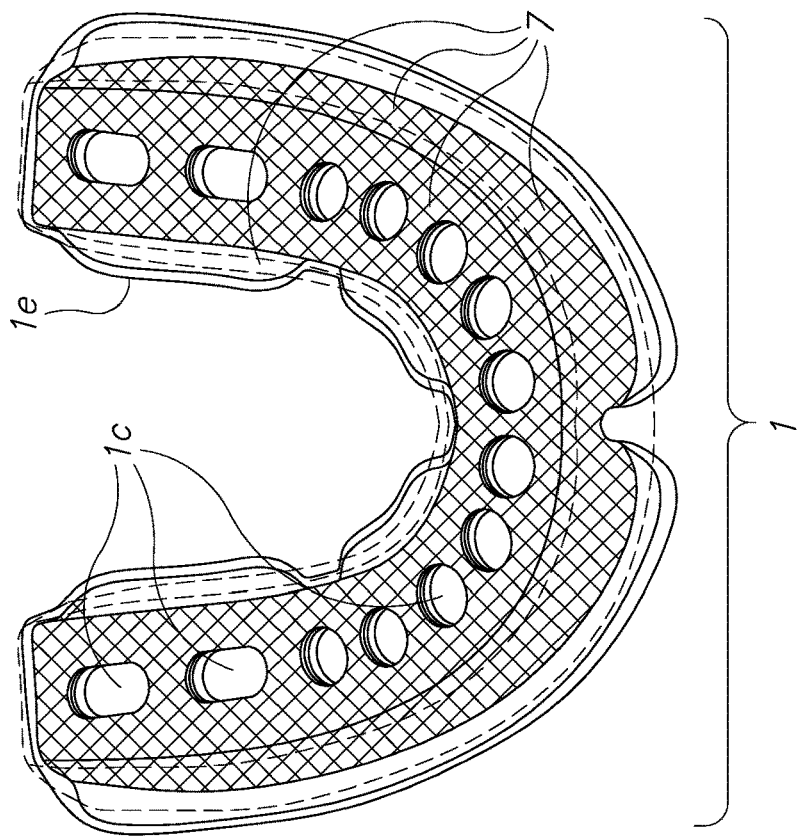
FIG. 5B is a view of an illustrative drape mold for an upper or lower jaw, showing the multi-layered drape materials from which the molded drapes are constructed, according to some embodiments.
Figure 5A:
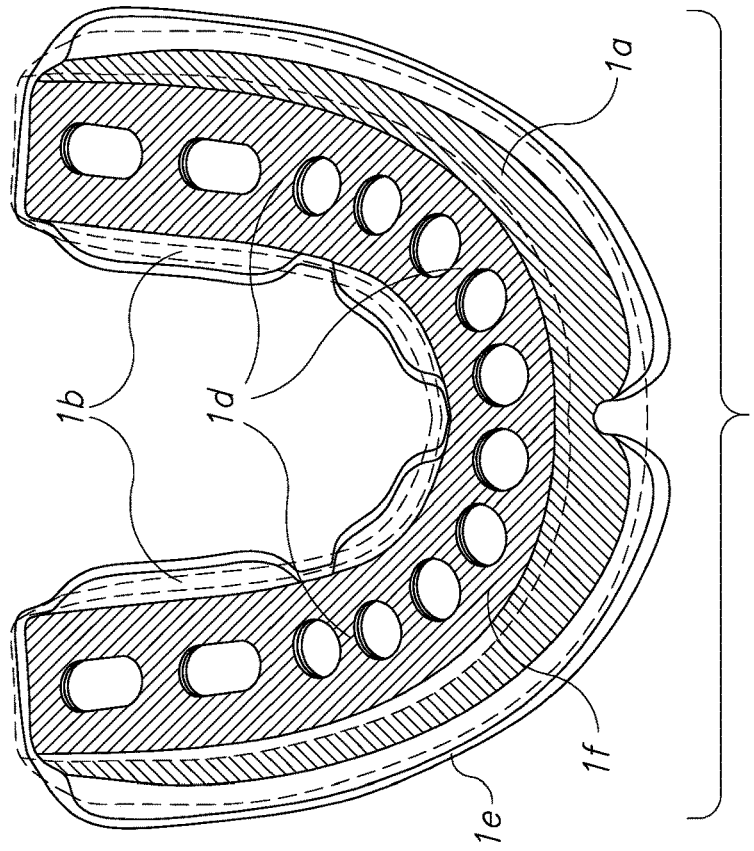
FIG. 5A is a view of an illustrative drape mold for an upper or lower jaw, showing the multi-layered drape materials from which the molded drapes are constructed, according to some embodiments.

FIGS. 5A and 5B are views of examples of drape molds for the upper and lower jaws, showing the multi-layered drape materials from which the molded drapes are constructed, according to some embodiments. As can be seen, mesh layer 5 may be impregnated with curable material 7, for example a LSA resin (light cured adhesive material), optionally in selected positions, to enable selective catalisation of different areas of the oral drape 1. Mesh layer 5 may further include a photo initiator(s) in the curable resin to potentiate later light catalyzation and curing of the embedded resin. In further embodiments, the curable material may be impregnated in one or more of the outer layers, such as films 6a and 6b, optionally in selected positions, to enable selective catalisation of different areas of the oral drape 1.

FIGS. 6A and 6B, as well as FIGS. 7A to 7F, FIGS. 8A and 8B, and FIGS. 9A to 9C, are views of examples of a process by which teeth holes are inserted into the drape mold, according to some embodiments. As can be seen, primarily in FIGS. 6A and 6B, a hole puncher, for example a upper thermo-coupler 10 coupled with a upper punching jig 9, may be used to initially punch holes in mesh layer 5. Upper punching jig 9 may be coupled to upper heat punches 9a, and may use an upper heat punch plate 9b, and upper heat punch set screws 9c. Further a lower heat punching jig 11 may be used, optionally with a lower heat punches 11a and lower heat punch plate 11b in conjunction with the upper punch jig 9, to produce the punch holes and weld seal the edges of the punch holes in the mesh layer and two outer film layers 6a and 6b, optionally where both upper and lower punch jigs are inserted together using frame jig 15.

As can be seen in FIGS. 7A and 7B, upper heat punching jig 9 may include an upper thermo-couplers 10 within upper heat punching plate 9b. Further, lower heat punching jig 11 may include a lower thermo-couplers 12 within lower heat punching plate 11b. As can be seen in FIGS. 7C and 7D, the respective upper and lower jigs may include respectively upper heat punches 9a and lower heat punches 11a. As can be seen in FIG. 7E, the upper thermo-couplers 10 may be used to selectively heat each of the upper punches 9a of the upper heat punch plate 9b. Similarly, lower thermo-couplers 12 may be used to selectively heat each of the lower punches 11a of the lower heat punch plate 11b.

Figure 8A:
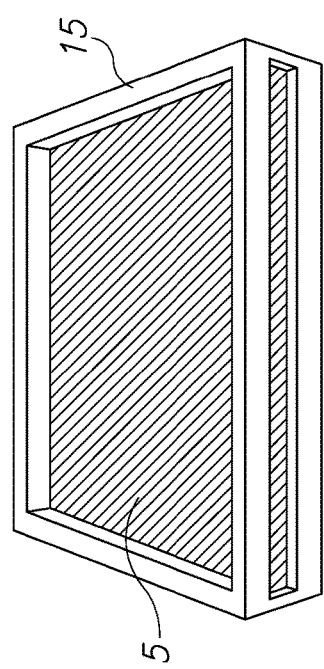
FIG. 8A is a view illustrating inserting teeth holes into drape molds, at a stage of manufacture, using a multi layered material, according to some embodiments.
Figure 8B:
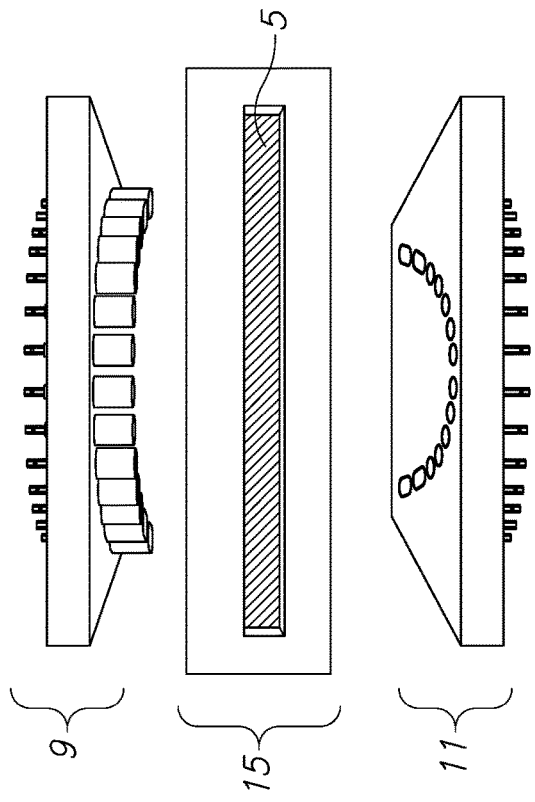
FIG. 8B is a view illustrating inserting teeth holes into drape molds, at a stage of manufacture, using a multi layered material, according to some embodiments.
Figure 8C:
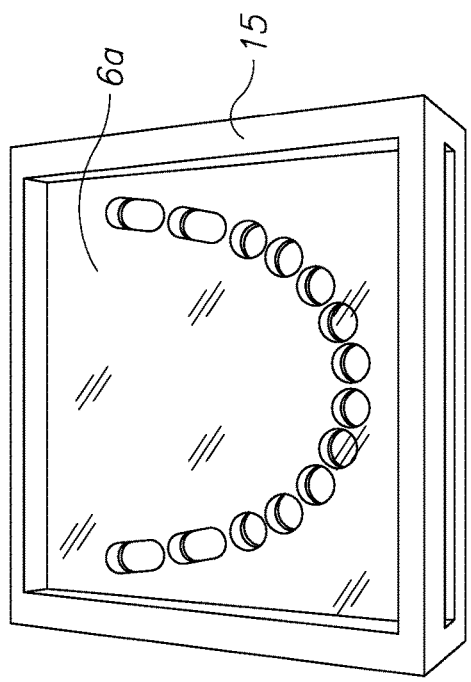
FIG. 8C is a view illustrating inserting teeth holes into drape molds, at a stage of manufacture, using a multi layered material, according to some embodiments.
Figure 8D:
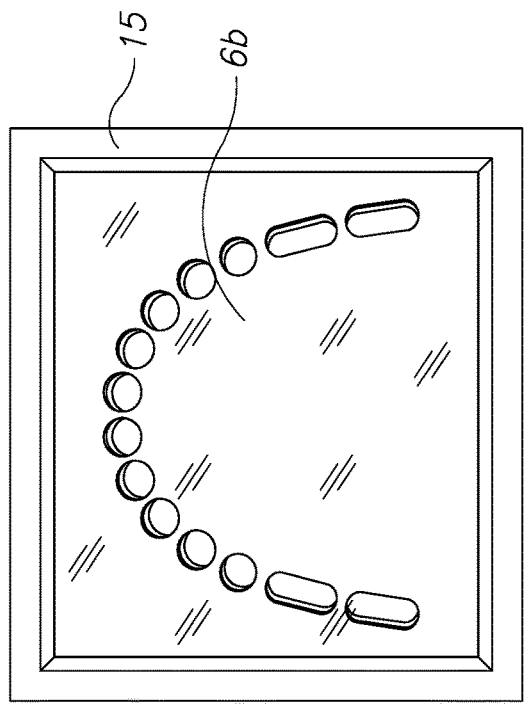
FIG. 8D is a view illustrating inserting teeth holes into drape molds, at a stage of manufacture, using a multi layered material, according to some embodiments.

FIGS. 8A and 8B are views of examples of the heat punching and welding of the cut edges of the teeth holes 5a in the mesh layer 5 that has been inserted into the frame jig 15. FIGS. 8C and 8D are upper and lower views of examples of the mesh layer 5 with punched holes 5a in the frame jig 15 to which have been inserted the upper film layer 6a and lower film layer 6b.

Figure 9B:
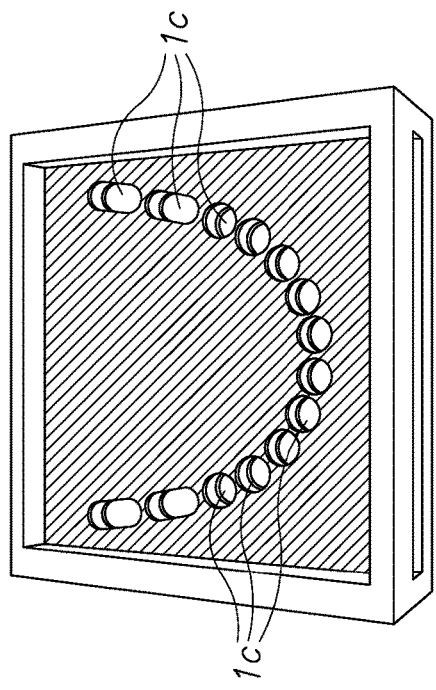
FIG. 9B is a drawing showing illustrative features of a multiple layer drape mold with teeth holes in a stage of manufacture, according to some embodiments.
Figure 9C:
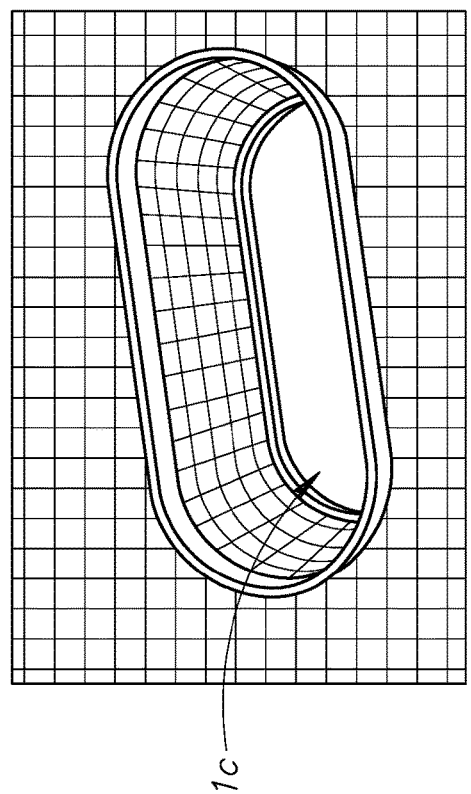
FIG. 9C is a drawing showing illustrative features of a multiple layer drape mold with teeth holes in a stage of manufacture, according to some embodiments.
Figure 9A:
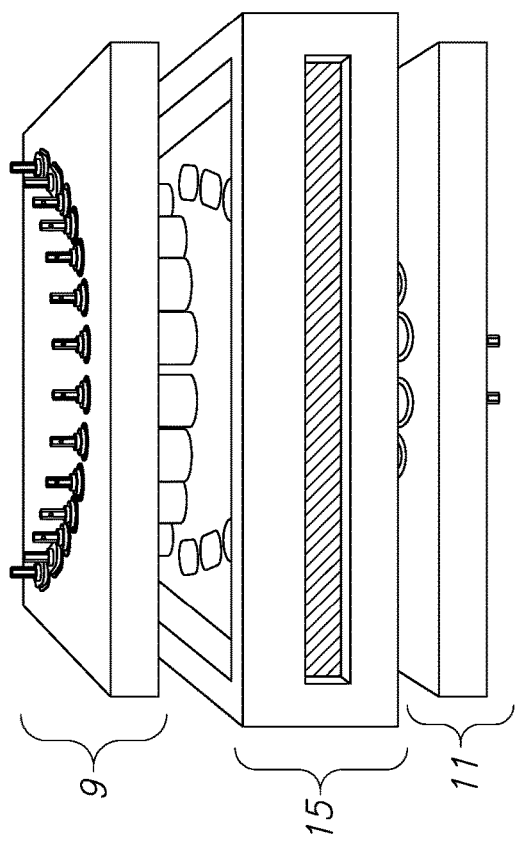
FIG. 9A is a drawing showing illustrative features of a multiple layer drape mold with teeth holes in a stage of manufacture, according to some embodiments.

As can be seen in FIGS. 9A to 9C, Upper Heat Punching Jig 9 and lower heat punching jig 11 may be used to punch holes and simultaneously weld seal the edges of the these holes into the upper film layer 6a and the lower film layer 6b, inside of frame jig 15, resulting in the formation of final Pre-cut out drape teeth holes with welded edges 1c.

FIGS. 10A and 10B are views of examples of multiple layered drape molds being constructed for using heat molding or heat setting, according to some embodiments. As can be seen, Upper Thermo-forming Jig 13a and Lower Thermo-forming Jig 13b may be used to produce an initial Three Dimensional Drape form 8

FIGS. 11A to 11D are views of examples of multiple layered drape mold heated punches 14a and 14b according to some embodiments. As can be seen, Upper Perimeter Heat Punch Jig 14a and Lower Perimeter Heat Punch Jig 14b may be used to produce a final Three Dimensional Drape form 1 within frame jig 15.

Figure 11A:
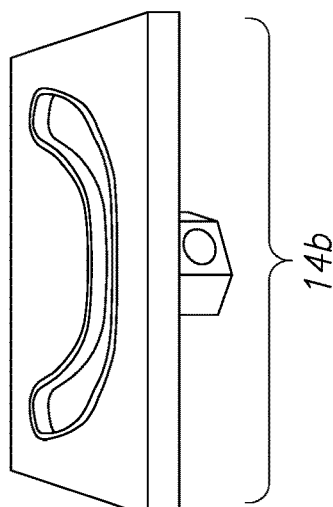
FIG. 11A is a view of an illustrative multiple layered drape mold being constructed using heat molding and punching, according to some embodiments.
Figure 11B:
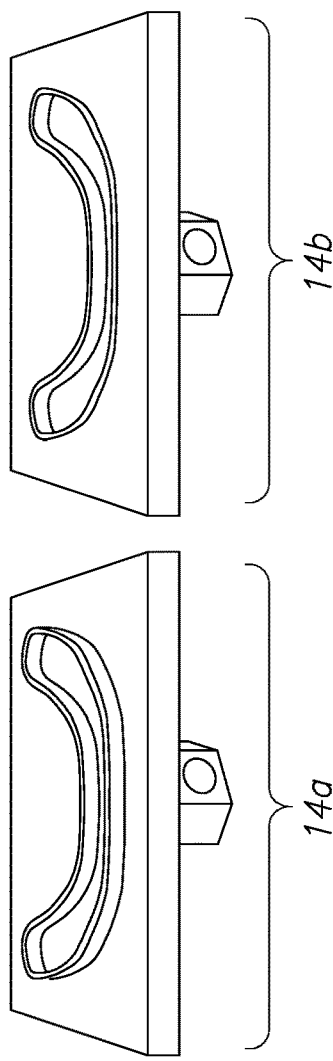
FIG. 11B is a view of an illustrative multiple layered drape mold being constructed using heat molding and punching, according to some embodiments.
Figure 11C:
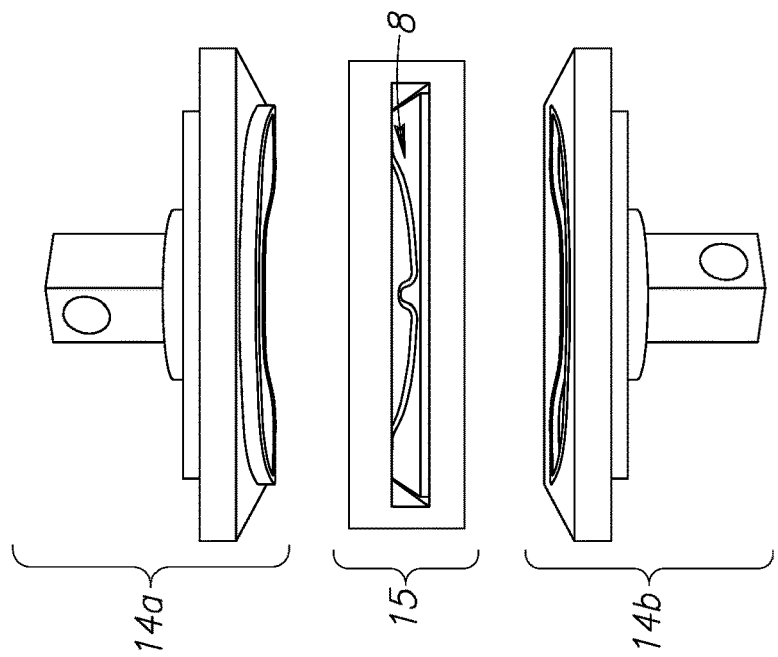
FIG. 11C is a view of an illustrative multiple layered drape mold being constructed using heat molding and punching, according to some embodiments.
Figure 11D:
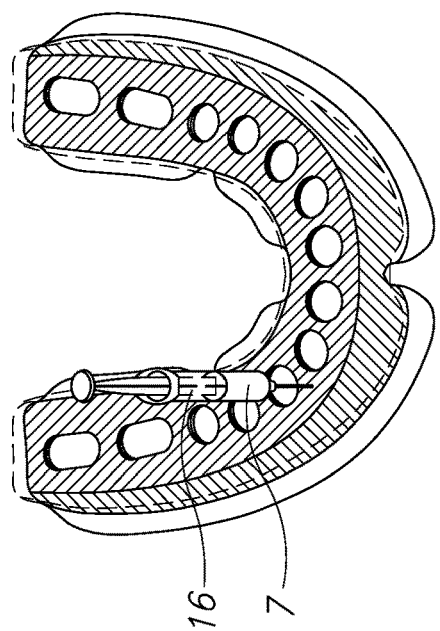
FIG. 11D is a view of an example of inserting a curing agent into a layer of the drape, according to some embodiments.
Figure 11E:
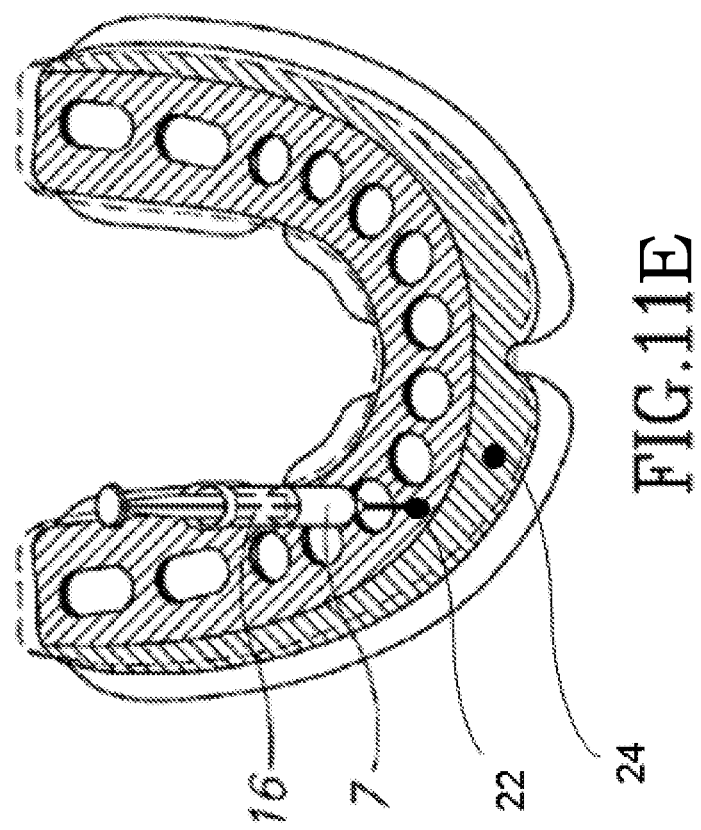
FIG. 11E is a view of an example of inserting a curing agent into a layer of the drape, according to some embodiments.

As can be seen in FIG. 11D, a syringe 16 such as a LCR syringe, may be used to deposit or inject curing materials, such as light curable resin 7, into the middle mesh layer 5 of the final drape form 1. The insertion of the curable resin may include injecting through an in-port 22 and allowing for the exit of excess curable resin through an out-port 24, such as illustrated in FIG. 11E.

Figure 12B:
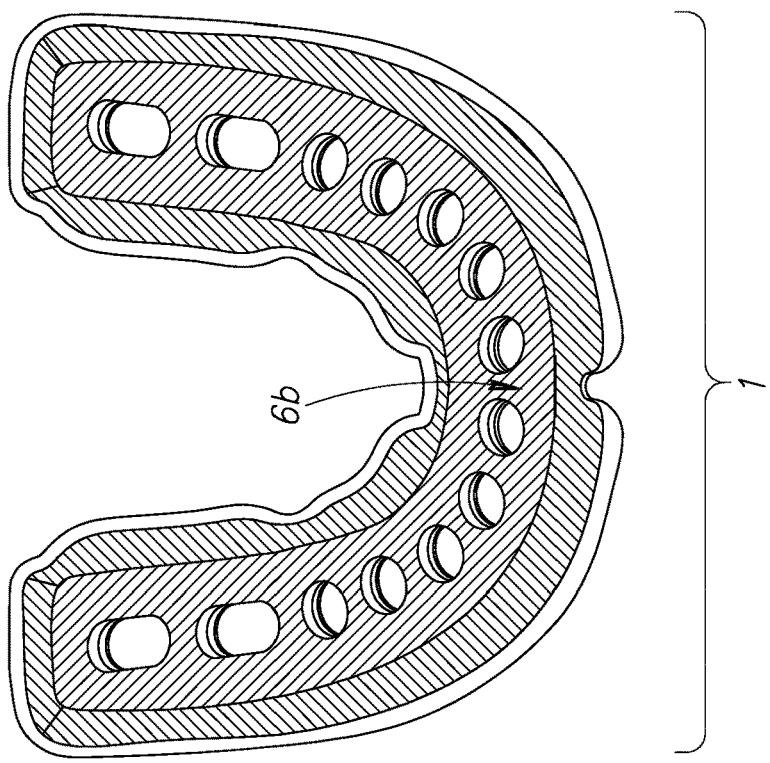
FIG. 12B is a view of an illustrative drape mold for an upper or lower jaw, showing the multi-layered drape materials from which the molded drape is constructed, according to some embodiments.
Figure 12A:
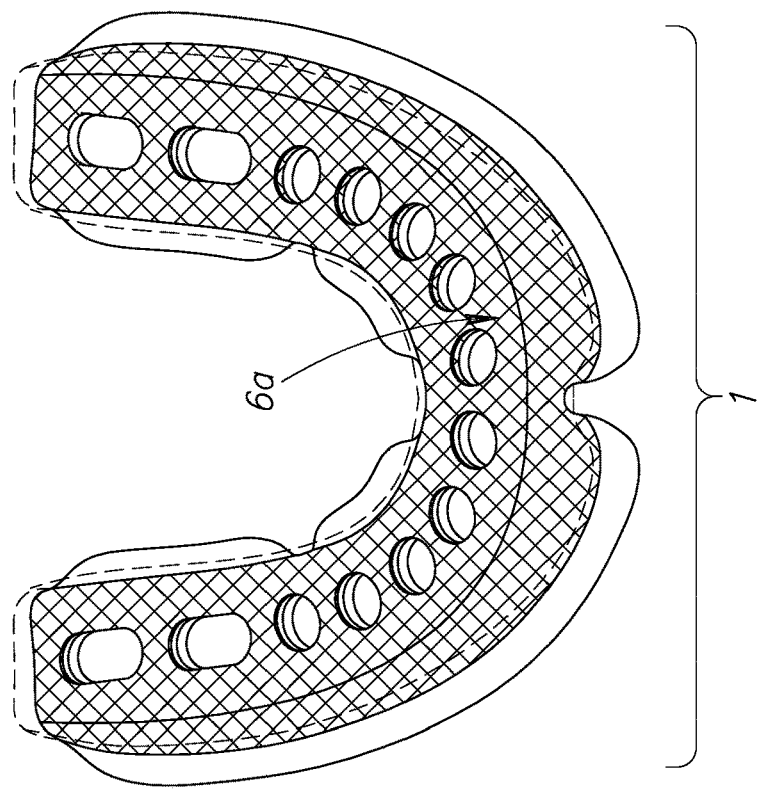
FIG. 12A is a view of an illustrative drape mold for an upper or lower jaw, showing the multi-layered drape materials from which the molded drape is constructed, according to some embodiments.

FIGS. 12A and 12B are respectively upper and lower views of examples of final drapes 1, showing the multi-layered drape materials, including mesh layer being surrounded respectively by films 6a and 6b, from which the molded drapes are constructed, according to some embodiments.

Figure 13A:
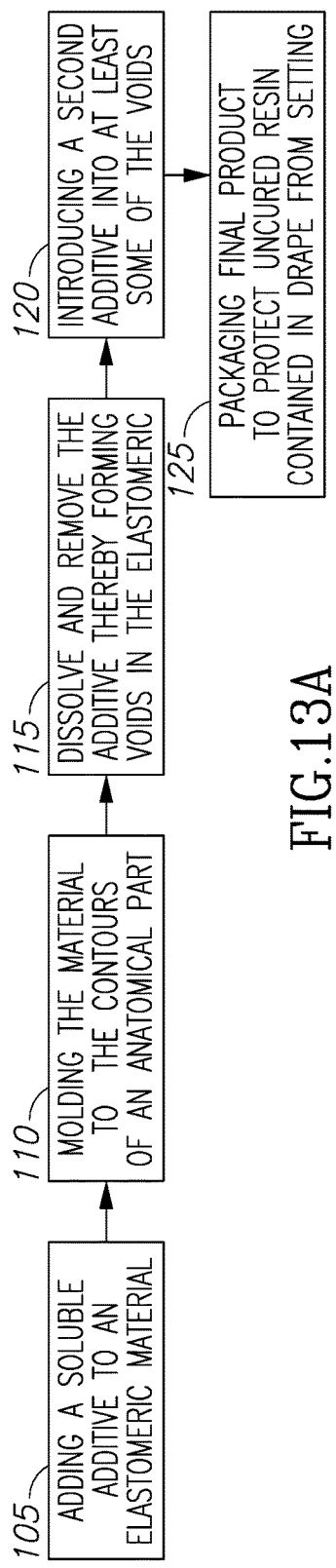
FIG. 13A is a flow diagram of an illustrative methods of manufacture, according to various embodiments.
Figure 13B:
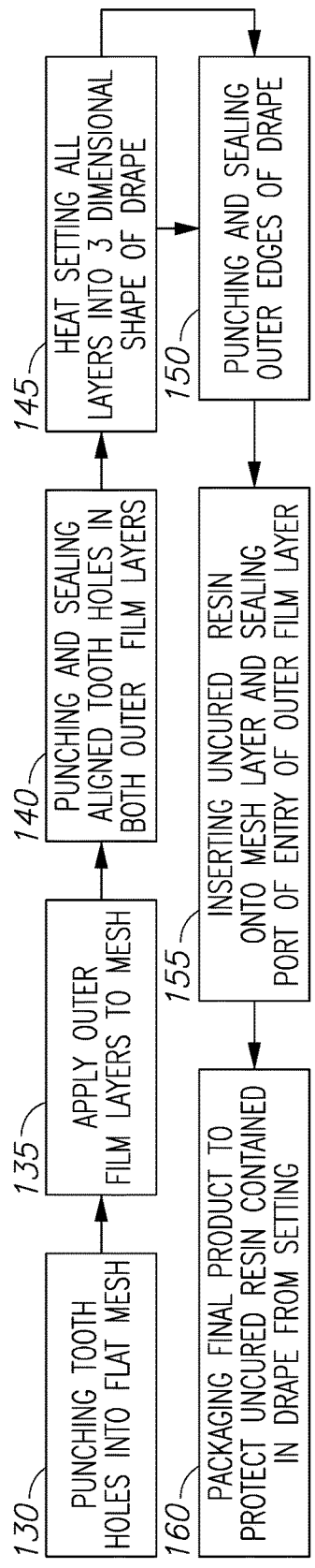
FIG. 13B is a flow diagram of an illustrative methods of manufacture, according to various embodiments.
Figure 13C:
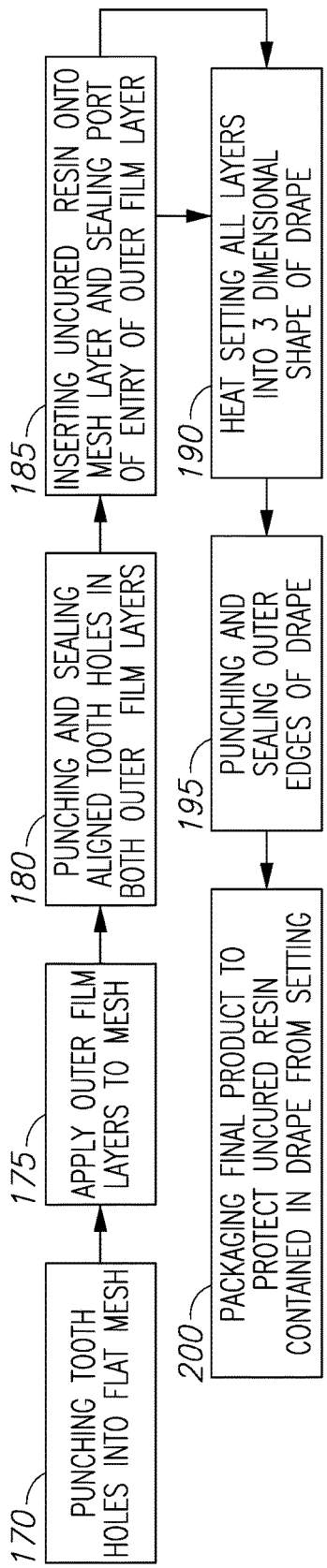
FIG. 13C is a flow diagram of an illustrative methods of manufacture, according to various embodiments.

FIGS. 13A-13C are flow diagrams of methods of manufacture, according to various embodiments. As can be seen in FIG. 13A, a drape manufacturing method, according to the first aspect of the present invention, may include: adding a soluble additive to an elastomeric material 105; molding the material to conform generally to the contours of an anatomical part 110; adding a solvent to dissolve and remove the additive thereby forming voids in the elastomeric material 115; and introducing a second additive into at least some of the voids 120. In some embodiments the final product may be packaged to protect the uncured resin contained in the drape from setting 125.

In this first method described, the soluble additive may comprise grit of any desired size for forming voids of a corresponding size. Preferably, the additive has a low or high melting point to cause flow or allow compression of material into a desired mold to cast the drape into a desired configuration. The second additive preferably comprises a curing agent, such as a light or UV light activated curing agent, wherein the drape may be tailored to the specific contours of a particular anatomical part and set/hardened in this configuration by activation of the curing agent. The adding of a second additive may include spraying, dipping, or injecting of the second additive to allow its introduction into the voids of the material. Preferably, addition and curing of the second additive retains the breathable properties of the drape while preserving its impermeability to fluids.

As can be seen in FIG. 13B, a method of drape manufacture, according to some embodiments, may include: securing under tension a flat mesh layer within a frame and punching (either with or without heat) the cut-out holes for the passage of teeth there-through 130; applying to both sides of the mesh the film-like outer layers 135; aligning a second punch that corresponds with the holes punched in the mesh, and punching (preferably with heat) corresponding holes through both outer film-like layers 140; sealing or setting (preferably with heat at the same time as the punch) the cut edges of the film-like outer layers, and heat setting all (e.g., three) layers (preferably through a thermo-forming process) into the desired three dimensional shape of the drape 145; punching and sealing (with our without heat) the outer edges of the drape 150; and inserting the curable resin through the outer layer (s) and onto the middle mesh layer 155. In some embodiments the final product may be packaged to protect the uncured resin contained in the drape from setting 160.

In some embodiments, the insertion of the LCR onto the mesh layer may be accomplished by several means of injection, including injecting through an in-port and allowing for the exit of excess LCR through an out-port of the anatomical drape. Multi-injection manual or automated jigs may also be set up so as to allow for even application and impregnation of the LCR onto the mesh and a final heat sealing process applied to anatomical mesh to seal off the multi-injection sites on the upper or lower outer film layers (or both) of the anatomical drape.

As can be seen in FIG. 13C, a method of drape manufacture, according to further embodiments, may include: securing under tension a flat mesh layer within a frame and punching (either with or without heat) the cut-out holes for the passage of teeth there-through 170; applying to both sides of the mesh the film-like outer layers 175; aligning a second punch that corresponds with the holes punched in the mesh, and punching (preferably with heat) corresponding holes through both outer film-like layers, and sealing (preferably with heat at the same time as the punch) the cut edges of the film-like outer layers 180; inserting the curable resin through the outer layer (s) and onto the middle mesh layer, and sealing the port(s) of entry of the outer firm layer 185; heat setting all three layers (optionally through a thermo-forming process) into the desired three dimensional shape of the drape 190; and punching and sealing (with our without heat) the outer edges of the drape 195. In some embodiments the final product may be packaged to protect the uncured resin contained in the drape from setting 197.

When punching or sealing is accomplished, it should be noted that duration of the punching and temperature of the punching tool(s) may vary dependent on which material is being punched and or its edges sealed. Additionally the duration of the punching and temperature of the punching tool(s) may vary dependent on the size or shape of the hole to be punched and or its edges sealed.

When punching or sealing is accomplished it should be noted that each individual punching element's temperature may be controlled to a specific range dependent on the size or shape of the hole to be punched and or sealed.

Heat setting duration and temperature both of the heating and cooling cycles of the process (thermo-forming) of the multiple layers of the drape may vary dependent of the materials used for each individual layer and in aggregate and the thickness of each individual layer and in aggregate.

For mass production of the drapes, according to some embodiments, multi-cavity molds with multiple punches may be used with large sheets or rolls of mesh and films, speed up manufacturing time and/or reduce manufacturing costs.

In accordance with some embodiments, the three dimensional shaping process using heat setting may require a slow increase in temperature and subsequent slow cooling. Since in some cases, the time required may be minutes, therefore a large scale manufacturing may involve a multi-cavity jig system.

In some embodiments, the heat shaping begins with softening of the strands of the mesh under the heat of an upper or lower or both side heated molds with subsequent slow cooling to fix the shaped strands into their new three dimensional form. By forming the three dimensional shape of the anatomical drape with this shaping process, the flat sheet mesh can be formed into a desired three dimensional shape substantially without the formation of any folds or creases of the mesh.

Also, as mentioned above, it is possible to heat form simultaneously a sandwich of a middle mesh layer with two outer film layers in the above heat shaping process. Although it is very much desirable to use film and mesh of the same material so as not to complicate the uniform heating and shaping of the mesh and film, this may not be possible as the optimal material for the mesh may be different than the optimal material for the two outer films. It is possible to obtain for example a heat shaped three dimensional form of all three layers by, for example, utilizing a polypropelene mesh middle layer and two outer polyurethane films.

According to additional embodiments a port may be provided for receiving a tool, such as a syringe for delivery of therapeutics to a treatment area.

According to additional embodiments, a kit of parts may be provided for installing an anatomical drape, the kit comprising a drape according to the first aspect of the present invention and a light source, optionally with at least one further drape and/or a therapeutic or other treatment source.

According to some embodiments, a dental oral drape is provided, that may include a flexible surgical arch shaped drape that is flexible to apply and to remove, that is designed to conform substantially to an anatomic area, and that is both liquid impermeable and gas permeable. In one example, the dental oral drape is designed to conform to the gum ridge anatomy, and has pre-configured cut-out holes of various shapes and diameters for insertion over and through the teeth (if the teeth are present), and for adaptation around or near to the gum line of the teeth, for example, as described in PCT application number WO 2013/039906 A1, by the same inventor. Of course drapes as described herein may be used to cover and/or contain treatment areas besides the oral area, for example, in or on other bodily limbs or parts.

In some embodiments, the device includes a dental oral drape component for protection against treatment materials (such as a whitening agent) applied to the teeth that may be exposed as well to the surrounding gum tissue of the teeth that are covered (contained) by an oral tooth and/or gum treatment device being used for a treatment cavity or cavities of a mouthpiece, for example, as described in PCT patent application number WO 2013/039906 A1, by the same inventor.

In some embodiments, the dental oral drape includes a treatment material layer on one or more surfaces, wherein the treatment material is suitable for neutralizing treatment materials.

In some embodiments, the device includes a dental oral drape component which includes a treatment layer on its inner surfaces for the delivery of one or more therapeutic treatment materials or medicinal materials to the gums or teeth.

In some embodiments the oral drape is formed from a variety of elastomeric materials such as but not limited to: TPE's (thermoplastic elastomers; TPU's (thermoplastic urethanes); elastomeric silicones (RTV, HTV, LSR) that are substantially both liquid impermeable and gas permeable (i.e., Breathable). For example, they may contain millions of micro-porosities per sq. cm. in their structure that are naturally formed during the mixing and molding process.

In some embodiments an additive material of various grit sizes that is soluble (e.g., using various solvents or even water) may be incorporated into the oral drape elastomeric materials during the drape formation process and prior to molding these elastomeric materials in a mold. In some examples, this additive may have a low or high melting point such that when either a low and/or high temperature molding process is utilized to form or mold the elastomeric material to a specific shape, these additive materials will remain embedded in the body structure of the elastomer during the molding process (e.g., which may require heating the elastomer to a either a low or high temperature to flow or compress the material into the desired mold).

Examples of the additive material may include but are not limited to various sodium salts, sodium bicarbonate, potassium salts, and sugars.

In a further fabrication step, the above described additive can then be removed from the structural matrix of the resultant molded elastomeric oral drape by dissolution in water or another solvent (e.g., at various temperatures and under various positive or negative air pressures, or electrically conductive conditions). This removal process of the additive particles results in a device whose three dimensional molded structure includes holes, which may be adapted to house additional elements. In one example, the drape device structure may resemble a "spongy weave like" matrix with voids or holes between the "spongy threads".

In a further fabrication step, a light curable material (for example, visible or UV light catalyzed) may then be impregnated into at least a portion of the resultant voids in the drape device substrate, created from gaps where the additive was located. For example, such a light curable material may be applied by spraying, rapidly dipping or injecting (or by means of another application process) the material onto the surface of the device so as to achieve a "scatter-like" pattern of the light curable material within the oral drape structure. In some examples, this partial impregnation of at least a portion of the surface of the oral drape device with the light curable material still allows for the material of the oral drape to retain its "breathable" characteristics (gas permeability) while preserving the devices' impermeability to fluids.

Examples of the light curable materials may include but are not limited to various blended mixtures of acrylate monomers, urethane acrylate oligomers, triacrylate cross linkers, plasticizers, and photo-initiators. Preferably this material is elastic and may have elongation properties, for example, of 10%-50%, or possibly even 100% or more.

According to some embodiments, this incorporated visible or UV "reinforcing matrix" can be utilized to custom shape the oral drape device to a specific patient's anatomy and substantially or partially immobilize this shape over the target area. In one example: The resultant three dimensional form can be draped over varying topography (e.g., each patient's mouth is unique) of the gum tissues (e.g., after first being pulled over and through the teeth in the dentulous situation), and then selectively patted or stretched down over the anatomy to achieve a high level of conformity to the individual tissue topography. The incorporated light curable material can then be hardened around individual teeth and the gums around them by applying a readily available dental LED or UV light source to the material. In some examples the light curable materials may be selectively cured, for example by applying the light in a segmental manner to specific areas of the drape so as to immobilize the desired customized final shape to the target area.

In some embodiments, the manufacturing process herein described provides for using a stock sized pre-formed (molded) three dimensionally shaped drape device (e.g., that is non-custom made for a target anatomy) that can be readily and quickly adapted to each patient's specific anatomy to provide a "custom fit" to each patient's anatomy. Such a customized drape may provide a superior substantially semi-rigid barrier that can be used, for example, in the following applications.

The drape as described above may be used as a wound dressing or containment device (with or without impregnating the inner surface with a therapeutic) or as a delivery device itself (e.g., if an additional therapeutic agent is later impregnated on its inner surface as a coating in a later step of the manufacturing process) to hold a therapeutic in place onto the target area. Therapeutic applications include but are not limited to post-periodontal (gum) surgery, post-dental implant surgery, following deep debridement (cleaning) of the gum tissues (specifically the naturally occurring sulcus between the gum and teeth) of patients with gingivitis or periodontitis, oral apthous lesions, and oral viral lesions.

In further embodiments, the initial form of the oral drape may substantially contain the treatment material in a more effective manner on the target treatment area, and allow for a significantly longer duration, larger quantity and/or larger surface area application of the treatment material to the applied target area as compared to the known art. This may be advantageous to substantially prevent or limit saliva contamination (filled with pathogenic bacteria) and saliva washout (dilution of the therapeutic in the salivary fluid and its removal as is the case with the prior art).

According to some embodiments, the oral drape device may be placed over the teeth so as to expose the teeth to the oral cavity (if present) and substantially cover the surrounding gums after prior application (injecting) of a therapeutic treatment either onto the surface of the gum tissue, onto the tooth surface near the gum line, or into the natural (healthy or diseased) space (sulcus) between the gums and the teeth which often (i.e. prevalence rates of 50-70% in the adult population of industrialized nations) harbor pathogenic bacteria that cause gum disease (gingivitis and periodontitis). This improved exposure of the treatment material to the target treatment area may enable enhanced effectiveness in halting progression of the gum disease or aid in regeneration of healing tissue post-surgery that may reverse the disease state or promote healing of surgically incised tissue so as to bring the gums back to a state of health.

In further embodiments, if applied to the tooth structure near the gum line that may be covered by the oral drape whilst leaving the remainder of the tooth exposed to the oral cavity, the treatment material may aid in more effectively re-mineralizing the demineralized (eroded) tooth structure that typically causes temperature (hot and cold) sensitivity to the teeth of patients who have these tooth erosions.

In accordance with further embodiments, a drape device that has been pre-impregnated on its inner surface with a treatment material at the time of fabrication or prior to insertion in the mouth, may have substantially all the advantages of the embodiments described above, while additionally enabling delivery of the therapeutic treatment material effectively and safely to a target location. In some examples this may obviate the need to first apply a treatment material onto or into the tissue to be treated. Such an embodiment may enhance the prevention and/or minimization of saliva contamination (filled with pathogenic bacteria) and saliva washout (dilution of the therapeutic in the salivary fluid and its removal).

As mentioned above, in some embodiments, the elastomeric materials used to form the pre-formed body structure of the oral draping device may be engineered to be differentially permeable (permeable to oxygen to permit "breathing" of the tissue under it and yet impermeable to fluids so as to prevent saliva contamination and washout).

In still further embodiments the oral drape device described herein may enable application to a patient anatomy to act as a barrier to substantially prevent moisture contamination of the tooth structure by the surrounding soft tissues, thereby creating what is commonly known in the field of dentistry as a "dry field" (i.e. a substantially moisture-free work area), which is often a very important requirement for properly placing many dental restoratives (fillings etc.) into the teeth. In the currently described embodiment, application of the device may compliment and/or replace the typical rubber dam (typically a flat latex sheet drape), which is relatively cumbersome, time consuming to place (typically requires manually punching holes in it to expose the teeth, placement of a clamping device on one of the teeth to keep the rubber dam in place and often attachment of the rubber dam to an external frame to keep its otherwise loose unsupported sections away from the work area). The currently known rubber dam devices are typically uncomfortable for the patient and challenging for usage by the dentist for the above reasons.

In accordance with some embodiments, the oral drape device may be fabricated in full arch forms to expose all the teeth while covering the surrounding gums of the upper or lower dental arches. It can also be fabricated to cover segments (e.g., anterior or posterior) or fabricated to expose a single tooth or only a few teeth and cover the adjacent surrounding gum tissue.

In additional embodiments, the drape device may be applied outside of the oral cavity, for example, by molding the material to a different shape (such as a sleeve or cuff), for covering a body part (e.g., the knee, elbow, ankle, neck etc.), by manually adapting so as to conform portions of the material to the surfaces of that body part so as to achieve excellent conformity and a "custom fit" of the material to that body surface, and then hardening at least some of the impregnated light curable material incorporated in its surfaces so as to achieve a semi-rigid cast or drape.

In further embodiments the drape device may also be formed in stock sized molded sections (e.g., to cover a limb, a portion of a limb, or a portion of the torso) and so may be used to treat a body area. In one example the drape device may be used to treat skin burn victims by effectively covering and partially immobilizing the damaged body parts substantially (especially in areas where there is normally joint movement of that body part), without the need for applying heavy plaster-type casts. In another example this application may be used where a treatment material may have first been applied separately to the damaged tissue or the treatment material may have been applied to the inner surface of the device prior to placing and adapting the device in a "custom fit manner to the desired treatment area".

In still further embodiments, the treatment material to be applied with the drape device may be formulated so that its therapeutic effect is in a time released manner or the treatment material may be first inserted into a manually or electronically controlled pumping device that has first been placed on the treatment area surface and then covered with the therapeutic draping device of the present invention.

The foregoing description of the embodiments of the invention has been presented for the purposes of illustration and description. It is not intended to be exhaustive or to limit the invention to the precise form disclosed. It should be appreciated by persons skilled in the art that many modifications, variations, substitutions, changes, and equivalents are possible in light of the above teaching. It is, therefore, to be understood that the appended claims are intended to cover all such modifications and changes as fall within the true spirit of the invention.

What is claimed is:

1. A pre-formed three dimensional curable gum ridge drape that generally conforms to an anatomical part for covering one or more areas of a gum ridge and exposing a plurality of teeth including adjacent teeth, comprising a drape material including an elastomeric material that is stretchable and the gum ridge drape is capable of conforming to the contours of the gum ridge, the gum ridge drape including an unreacted curing agent selectively incorporated within a structure of the gum ridge drape, wherein after conforming to the contours of the gum ridge, activation of the curing agent selectively constrains elastic properties of the drape material to at least partially set the gum ridge drape in a fixed configuration conforming to the gum ridge, wherein the gum ridge drape covers a gum ridge; while exposing the adjacent teeth, wherein the gum ridge drape includes interdental tension bridges designed to fit into interproximal spaces between all adjacent teeth, wherein the gum ridge drape provides a circumferential fit around all exposed teeth; wherein the gum ridge drape covers only one gum ridge, upon stretching and curing, the gum ridge drape custom fits the treatment area of the gum ridge thereby replacing the need for a device having a clamping component.

2. The gum ridge drape of claim 1, wherein the drape material is liquid impermeable and gas permeable, both before and after curing.

3. The gum ridge drape of claim 1, wherein the drape includes holes for passage of the teeth there through.

4. The gum ridge drape of claim 1, wherein the curing agent is positioned in select areas of the gum ridge drape, between layers of the elastomeric material.

5. The gum ridge of claim 1, wherein the drape structure includes outer layers of the elastomeric material and a middle layer including the curing agent.

6. The gum ridge drape of claim 5 wherein the curing agent is a light curable agent including an acrylate monomer, a urethane acrylate oligomer, a tri-acrylate cross linker, a plasticizer, or a photo-initiator.

7. The gum ridge drape of claim 1, wherein the curing agent is activated by an external source selected from one or more of heat and light.

8. The gum ridge drape of claim 7, wherein the gum ridge drape includes a curable resin and a packaging to protect uncured resin contained in the drape from setting.

9. The gum ridge drape of claim 1, wherein one or more treatment material layers are included on at least one surface of the anatomical drape.

10. A kit of parts for installing a gum ridge drape, the kit comprising:
the gum ridge drape of claim 1, and
a UV light source.

11. The kit of claim 10, wherein the kit includes an additional gum ridge drape.

12. The kit of claim 10, wherein the kit includes a therapeutic treatment source.

13. The gum ridge drape of claim 1, wherein the gum ridge drape includes an in-port for insertion of the curable resin into a middle layer of the gum ridge drape and an out-port allowing for the exit of an excess of the curable resin.

14. The gum ridge drape of claim 1, wherein the anatomical drape is constructed from multiple layers of the elastomeric material.

15. The gum ridge drape of claim 1, wherein the gum ridge drape is impermeable to hydrogen peroxide.

16. The gum ridge drape of claim 1, wherein the curing agent is activated by heat.

17. The gum ridge drape of claim 1, wherein the curing agent is activated by visible light and the drape structure includes an outer layer that is transparent.

18. A curable oral drape for covering a treatment area of an oral cavity, the oral drape comprising a drape structure including outer layers of an elastomeric material and a middle layer including a curing agent, the elastomeric material capable of conforming to the contours of an oral anatomical part, and selective activation of the curing agent causes selective hardening of the drape structure to at least partially set the oral drape in a configuration conforming to the oral anatomical part, the set oral drape is gas permeable but liquid impermeable; wherein the oral drape has holes for the passage of individual teeth therethrough, wherein a crown portion of the individual teeth is exposed after covering the treatment area with the oral drape.

19. A pre-formed three dimensional curable anatomical drape comprising elastomeric outer layers, a middle layer including an uncured curable resin, and teeth holes through the outer layers and the middle layer, wherein the anatomical drape can be stretch to conform margins of the individually stretched teeth holes to anatomical gum lines of the teeth and maintain the margins of the stretched positions of the teeth holes by curing the curable resin and hardening the anatomic drape, wherein teeth are exposed through the anatomical drape, and the anatomical drape covers a gum surrounding the exposed teeth.

20. The curable anatomical drape of claim 19, wherein the uncured curable resin is a visible light curable resin, and one of the outer layers is transparent so that the visible light curable resin can be hardened around individual teeth with a dental visible light source.

* * * * *